(12) United States Patent (10) Patent No.: US 9,050,296 B2
Lindner (45) Date of Patent: Jun. 9, 2015

(54) METHODS FOR TREATING METABOLIC SYNDROME WITH CTHRC1 POLYPEPTIDE

(71) Applicant: Volkhard Lindner, South Portland, ME (US)

(72) Inventor: Volkhard Lindner, South Portland, ME (US)

(73) Assignee: MAINE MEDICAL CENTER, Scarborough, ME (US)

( * ) Notice: Subject to any disclaimer, the term of this patent is extended or adjusted under 35 U.S.C. 154(b) by 0 days.

(21) Appl. No.: 13/934,455

(22) Filed: Jul. 3, 2013

(65) Prior Publication Data

US 2014/0011737 A1 Jan. 9, 2014

Related U.S. Application Data

(60) Provisional application No. 61/667,713, filed on Jul. 3, 2012.

(51) Int. Cl.
*A61P 3/04* (2006.01)
*A61P 3/06* (2006.01)
*A61P 3/08* (2006.01)
*A61P 3/10* (2006.01)
*A61P 9/12* (2006.01)
*A61K 38/17* (2006.01)
*G01N 33/53* (2006.01)
*A01K 67/027* (2006.01)
*C07K 16/18* (2006.01)
*G01N 33/68* (2006.01)
*C07K 14/78* (2006.01)
*C07K 14/435* (2006.01)
*C07K 14/47* (2006.01)
*A61K 48/00* (2006.01)

(52) U.S. Cl.
CPC ............ A61K 38/1709 (2013.01); G01N 33/53 (2013.01); A01K 67/0276 (2013.01); C07K 14/47 (2013.01); C07K 16/18 (2013.01); G01N 33/6893 (2013.01); C07K 2317/34 (2013.01); G01N 2800/04 (2013.01); G01N 2800/50 (2013.01); A61K 48/005 (2013.01); C07K 14/78 (2013.01); A01K 2217/075 (2013.01); A01K 2227/105 (2013.01); A01K 2267/0362 (2013.01)

(58) Field of Classification Search
None
See application file for complete search history.

(56) References Cited

U.S. PATENT DOCUMENTS

| | | | |
|---|---|---|---|
| 5,399,346 | A | 3/1995 | Anderson et al. |
| 6,630,325 | B1 | 10/2003 | Lindner et al. |
| 2002/0161211 | A1 | 10/2002 | Lindner et al. |
| 2005/0147602 | A1* | 7/2005 | Lindner .................... 424/130.1 |

OTHER PUBLICATIONS

Stohn et al, 2012 (PLOS One. 10(7): 1-12).*
Wells (1990) Biochemistry 29(37): 8509-8517.*
Ngo et al (1994) "The Protein Folding Problem and Tertiary Structure Prediction, Chapter 14: Computational Complexity Protein Structure Prediction, and the Levinthal Paradox" pp. 433-440 and 492-495 only.*
Bork (2000) Genome Research 10:398.*
Skolnick et al (2000) Trends in Biotech. 18(1): 34.*
Doerks et al (1998) Trends in Genetics 14(6): 248.*
Brenner (1999) Trends in Genetics 15(4): 132.*
Anderson. "Prospects for Human Gene Therapy." *Science*. 226.4273(1984):401-409.
Atkinson et al. "Potential Mechanisms and Consequences of Cardiac Triacylglycerol Accumulation in Insulin-Resistant Rats." *Am. J. Physiol. Endocrinol. Metab*. 284.5(2003):E923-E930.
Benton et al. "Screening λgt Recombinant Clones by Hybridization to Single Plaques in situ." *Science*. 196.4286(1977):180-182.
Blömer et al. "Highly Efficient and Sustained Gene Transfer in Adult Neurons with a Lentivirus Vector." *J. Virol*. 71.9(1997):6641-6649.
Brigham et al. "In vivo Transfection of Murine Lungs with a Functioning Prokaryotic Gene Using a Liposome Vehicle." *Am. J. Med. Sci*. 298.4(1989):278-281.
Cayouette et al. "Adenovirus-Mediated Gene Transfer of Ciliary Neurotrophic Factor can Prevent Photoreceptor Degeneration in the Retinal Degeneration (rd) Mouse." *Hum. Gene Ther*. 8.4(1997):423-430.
Ch'ng et al. "Antisense RNA Complementary to 3' Coding and Noncoding Sequences of Creatine Kinase is a Potent Inhibitor of Translation in vivo." *PNAS*. 86.24(1989):10006-10010.
Chou et al. "Quantitative Analysis of Dose-Effect Relationships: The Combined Effects of Multiple Drugs or Enzyme Inhibitors." *Adv. Enzyme Regul*. 22(1984):27-55.
Christoffersen et al. "Cardiac Lipid Accumulation Associated with Diastolic Dysfunction in Obese Mice." *Endocrinol*. 144.8(2003):3483-3490.
Ciocca et al. "The Pituitary Cleft of the Rat: An Electron Microscopic Study." *Tissue Cell*. 10.4(1978):725-733.
Cornetta et al. "Gene Transfer into Primates and Prospects for Gene Therapy in Humans." *Prog. Nucleic Acid Res. Mol. Biol*. 36(1989):311-322.
Eglitis et al. "Retroviral Vectors for Introdcution of Genes into Mammalian Cells." *Biotechniques*. 6.7(1988):608-614.
Felgner et al. "Lipofection: A Highly Efficient, Lipid-Mediated DNA-Transfection Procedure." *PNAS*. 84.21(1987):7413-7417.
Friedmann. "Progress Toward Human Gene Therapy." *Science*. 244.4910(1989):1275-1281.

(Continued)

*Primary Examiner* — Zachary Howard
(74) *Attorney, Agent, or Firm* — Mintz Levin Cohn Ferris Glovsky and Popeo, P.C.; David G. Conlin

(57) ABSTRACT

The present invention features compositions and methods for treating and preventing a metabolic syndrome featuring the collagen triple helix repeat containing-1 (Cthrc1) protein.

9 Claims, 9 Drawing Sheets

(56) References Cited

OTHER PUBLICATIONS

Grunstein et al. "Colony Hybridization: A Method for the Isolation of Cloned DNAs that Contain a Specific Gene." *PNAS*. 72.10(1975):3961-3965.
Hada et al. "Selective Purification and Characterization of Adiponectin Multimer Species from Human Plasma." *Biochem. Biophys. Res. Commun*. 356.2(2007):487-493.
Johnson. "Gene Therapy for Cystic Fibrosis." *Chest*. 107.52(1995):775-83S.
Kameda. "Occurrence of Colloid-Containing Follicles in the pars distalis of Pituitary Glands from Aging Guinea Pigs." *Cell Tissue Res*. 263.1(1991):115-124.
Kimmel. "Identification and Characterization of Specific Clones: Strategy for Confirming the Validity of Presumptive Clones." *Methods Enzymol*. 152(1987):507-511.
Kimura et al. "Cthrc1 is a Positive Regulator of Osteoblastic Bone Formation." *PLoS One*. 3.9(2008):e3174.
Lara-Castro et al. "Adiponectin Multimeric Complexes and the Metabolic Syndrome Trait Cluster." *Diabetes*. 55.1(2006):249-259.
Larman et al. "Distinct Bone Morphogenetic Proteins Activate Indistinguishable Transcriptional Responses in Nephron Epithelia Including Notch Target Genes." *Cell Signal*. 24.1(2012):257-264.
Le Gal La Salle et al. "An Adenovirus Vector for Gene Transfer into Neurons and Glia in the Brain." *Science*. 259.5097(1993):988-990.
LeClair et al. "Cthrc1 is a Novel Inhibitor of Transforming Growth Factor-β Signaling and Neointimal Lesion Formation." *Circ. Res*. 100.6(2007):826-833.
Lee et al. "Endocrine Regulation of Energy Metabolism by the Skeleton." *Cell*. 130.3(2007):456-469.
Lihn et al. "Adiponectin: Action, Regulation and Association to Insuling Sensitivity." *Obese Rev*. 6.1(2005):13-21.
McGavock et al. "Adiposity of the Heart, Revisited." *Ann. Intern. Med*. 144.7(2006):517-524.
Miller et al. "Improved Retroviral Vectors for Gene Transfer and Expression." *Biotechniques*. 7.9(1989):980-990.
Miller. "Retrovirus Packaging Cells." *Hum. Gene Ther*. 1.1(1990):5-14.
Miyoshi et al. "Stable and Efficient Gene Transfer into the Retina Using an HIV-based Lentiviral Vector." *PNAS*. 94.19(1997):10319-10323.
Moen. "Directions in Gene Therapy." *Blood Cells*. 17.2(1991):407-416.
Naldini et al. "In Vivo Gene Delivery and Stable Transduction of Nondividing Cells by a Lentiviral Vector." *Science*. 272.5259(1996):263-267.
NCBI Accession No. NM_001256099, Jun. 30, 2012.
NCBI Accession No. NM_138455, Jun. 30, 2012.
Ogawa et al. "Histochemical Study of Follicles in the Senescent Porcine Pituitary Gland." *Arch. Histol. Cytol*. 59.5(1996):467-478.
Ono et al."Plasmid DNAs Directly Injected into Mouse Brain with Lipofection can be Incorporated and Expressed by Brain Cells." *Neurosci. Lett*. 117.3(1990):259-263.
Park et al. "Biogenesis and Transport of Secretory Granules to Release Site in Neuroendocrine Cells." *J. Mol. Neurosci*. 37.2(2009):151-159.
Park et al. "Carboxypeptidase E Cytoplasmic Tail-Driven Vesicle Transport is Key for Activity-Dependent Secretion of Peptide Hormones." Mol. Endocrinol. 22.4(2008):989-1005.
Pyagay et al. "Collagen Triple Helix Repeat Containing 1, a Novel Secreted Protein in Injured and Diseased Arteries, Inhibits Collagen Expression and Promotes Cell Migration." *Circ. Res*. 96.2(2005):261-268.
Rattan et al. "Protein Synthesis, Posttranslational Modifications, and Aging." *Ann N.Y. Acad. Sci*. 663(1992):48-62.
Rodrigues et al. "Metabolic Disturbances in Diabetic Cardiomyopathy." *Mol. Cell. Biochem*. 180.1-2(1998):53-57.
Rodrigues et al. "Myocardial Substrate Metabolism: Implications for Diabetic Cardiomyopathy." *J. Mol. Cell. Cardiol*. 27.1(1995):169-179.
Rosenberg et al. "Gene Transfer into Humans: Immunotherapy of Patients with Advanced Melanoma, Using Tumor-Infiltrating Lymphocytes Modified by Retroviral Gene Transduction." *N. Engl. J. Med*. 323.9(1990):570-578.
Scharfmann et al. "Long-Termn in vivo Expression of Retrovirus-Mediated Gene Transfer in Mouse Fibroblast Implants." *PNAS*. 88.11(1991):4626-4630.
Seifter et al. "Analysis for Protein Modifications and Nonprotein Cofactors." *Methods Enzymol*. 182(1990):626-646.
Sharp. "Gene Therapy." *Lancet*. 337.7852(1991):1277-1278.
Straubinger et al. "Liposomes as Carriers for Intracellular Delivery of Nucleic Acids." *Methods Enzymol*. 101(1983):512-527.
Tolstoshev et al. "Gene Expression Using Retroviral Vectors." *Curr. Opin. Biotechnol*. 1.1(1990):55-61.
Wahl et al. "Molecular Hybridization of Immobilized Nucleic Acids: Theoretical Concepts and Practical Considerations." *Methods Enzymol*. 152(1987):399-407.
Wold. "Posttranslational Protein Modifications: Perspectives and Prospects." *Posttranslation Covalent Modifications of Proteins*. New York: Academic Press. (1983):1-12.
Wolff et al. "Direct Gene Transfer into Mouse Muscle in Vivo." *Science*. 249.4949(1990):1465-1468.
Wong et al. "Identification and Characterization of CTRP9, a Novel Secreted Glycoprotein, from Adipose Tissue that Reduces Serum Glucose in Mice and Forms Heterotrimers with Adiponectin." *FASEB J*. 23.1(2009):241-258.
Wu et al. "Receptor-Mediated Gene Delivery and Expression in vivo." *J. Biol. Chem*. 263.29(1988):14621-14624.
Wu et al. "Targeting Genes: Delivery and Persistent Expression of a Foreign Gene Driven by Mammalian Regulatory Elements in Vivo." *J. Biol. Chem*. 264.29(1989):16985-16987.
Yamamoto et al. "Cthrc1 Selectively Activates the Planar Cell Polarity Pathway of Wnt Signaling by Stabilizing the Wnt-Receptor Complex." *Dev. Cell*. 15.1(2008):23-36.

* cited by examiner

```
                              SEQUENCE LISTING

<160> NUMBER OF SEQ ID NOS: 14

<210> SEQ ID NO 1
<211> LENGTH: 243
<212> TYPE: PRT
<213> ORGANISM: Homo sapiens

<400> SEQUENCE: 1

Met Arg Pro Gln Gly Pro Ala Ala Ser Pro Gln Arg Leu Arg Gly Leu
1               5                   10                  15

Leu Leu Leu Leu Leu Leu Gln Leu Pro Ala Pro Ser Ser Ala Ser Glu
            20                  25                  30

Ile Pro Lys Gly Lys Gln Lys Ala Gln Leu Arg Gln Arg Glu Val Val
        35                  40                  45

Asp Leu Tyr Asn Gly Met Cys Leu Gln Gly Pro Ala Gly Val Pro Gly
    50                  55                  60

Arg Asp Gly Ser Pro Gly Ala Asn Val Ile Pro Gly Thr Pro Gly Ile
65                  70                  75                  80

Pro Gly Arg Asp Gly Phe Lys Gly Glu Lys Gly Glu Cys Leu Arg Glu
                85                  90                  95

Ser Phe Glu Glu Ser Trp Thr Pro Asn Tyr Lys Gln Cys Ser Trp Ser
            100                 105                 110

Ser Leu Asn Tyr Gly Ile Asp Leu Gly Lys Ile Ala Glu Cys Thr Phe
        115                 120                 125

Thr Lys Met Arg Ser Asn Ser Ala Leu Arg Val Leu Phe Ser Gly Ser
    130                 135                 140

Leu Arg Leu Lys Cys Arg Asn Ala Cys Cys Gln Arg Trp Tyr Phe Thr
145                 150                 155                 160

Phe Asn Gly Ala Glu Cys Ser Gly Pro Leu Pro Ile Glu Ala Ile Ile
                165                 170                 175

Tyr Leu Asp Gln Gly Ser Pro Glu Met Asn Ser Thr Ile Asn Ile His
            180                 185                 190

Arg Thr Ser Ser Val Glu Gly Leu Cys Glu Gly Ile Gly Ala Gly Leu
        195                 200                 205

Val Asp Val Ala Ile Trp Val Gly Thr Cys Ser Asp Tyr Pro Lys Gly
    210                 215                 220

Asp Ala Ser Thr Gly Trp Asn Ser Val Ser Arg Ile Ile Ile Glu Glu
225                 230                 235                 240

Leu Pro Lys

<210> SEQ ID NO 2
<211> LENGTH: 1279
<212> TYPE: DNA
<213> ORGANISM: Homo sapiens

<400> SEQUENCE: 2
gggagggaga gaggcgcgcg ggtgaaaggc gcattgatgc agcctgcggc ggcctcggag      60
cgcggcggag ccagacgctg accacgttcc tctcctcggt ctcctccgcc tccagctccg     120
cgctgcccgg cagccgggag ccatgcgacc ccagggcccc gccgcctccc cgcagcggct     180
ccgcggcctc ctgctgctcc tgctgctgca gctgcccgcg ccgtcgagcg cctctgagat     240
ccccaagggg aagcaaaagg cgcagctccg gcagagggag gtggtggacc tgtataatgg     300
```

| | |
|---|---|
| aatgtgctta caagggccag caggagtgcc tggtcgagac gggagccctg gggccaatgg | 360 |
| cattccgggt acacctggga tcccaggtcg ggatggattc aaaggagaaa aggggggaatg | 420 |
| tctgagggaa agctttgagg agtcctggac acccaactac aagcagtgtt catggagttc | 480 |
| attgaattat ggcatagatc ttgggaaaat tgcggagtgt acatttacaa agatgcgttc | 540 |
| aaatagtgct ctaagagttt tgttcagtgg ctcacttcgg ctaaaatgca gaaatgcatg | 600 |
| ctgtcagcgt tggtatttca cattcaatgg agctgaatgt tcaggacctc ttcccattga | 660 |
| agctataatt tatttggacc aaggaagccc tgaaatgaat tcaacaatta atattcatcg | 720 |
| cacttcttct gtggaaggac tttgtgaagg aattggtgct ggattagtgg atgttgctat | 780 |
| ctgggttggt acttgttcag attacccaaa aggagatgct tctactggat ggaattcagt | 840 |
| ttctcgcatc attattgaag aactaccaaa ataaatgctt taattttcat ttgctacctc | 900 |
| tttttttatt atgccttgga atggttcact taaatgacat tttaaataag tttatgtata | 960 |
| catctgaatg aaaagcaaag ctaaatatgt ttacagacca aagtgtgatt tcacactgtt | 1020 |
| tttaaatcta gcattattca ttttgcttca atcaaaagtg gtttcaatat ttttttagt | 1080 |
| tggttagaat actttcttca tagtcacatt ctctcaacct ataatttgga atattgttgt | 1140 |
| ggtcttttgt tttttctctt agtatagcat ttttaaaaaa atataaaagc taccaatctt | 1200 |
| tgtacaattt gtaaatgtta agaattttt ttatatctgt taaataaaaa ttatttccaa | 1260 |
| caaccttaat atctttaaa | 1279 |

<210> SEQ ID NO 3
<211> LENGTH: 1214
<212> TYPE: DNA
<213> ORGANISM: Homo sapiens

<400> SEQUENCE: 3

| | |
|---|---|
| agaaggttta aggccggaaa gggaaatgaa ggggcccggc gctaaccctc taaggacctg | 60 |
| ttttgcttct gtttaaacca aatgggcagt ctgtcattac acacaccctg ggtcttcata | 120 |
| tgtggccgcc aggtaggagc atcacagtca agctacggga gaaaacagtt tccaggaaac | 180 |
| tggaaatgaa cggcccgagt gctttccagg ggctcatctg tgggaagtat aatggaatgt | 240 |
| gcttacaagg gccagcagga gtgcctggtc gagacgggag ccctgggcc aatggcattc | 300 |
| cgggtacacc tgggatccca ggtcgggatg gattcaaagg agaaagggg gaatgtctga | 360 |
| gggaaagctt tgaggagtcc tggacaccca actacaagca gtgttcatgg agttcattga | 420 |
| attatggcat agatcttggg aaaattgcgg agtgtacatt tacaaagatg cgttcaaata | 480 |
| gtgctctaag agttttgttc agtggctcac ttcggctaaa atgcagaaat gcatgctgtc | 540 |
| agcgttggta tttcacattc aatggagctg aatgttcagg acctcttccc attgaagcta | 600 |
| taatttattt ggaccaagga agccctgaaa tgaattcaac aattaatatt catcgcactt | 660 |
| cttctgtgga aggactttgt gaaggaattg gtgctggatt agtggatgtt gctatctggg | 720 |
| ttggtacttg ttcagattac ccaaaaggag atgcttctac tggatggaat tcagtttctc | 780 |
| gcatcattat tgaagaacta ccaaaataaa tgctttaatt ttcatttgct acctcttttt | 840 |
| ttattatgcc ttggaatggt tcacttaaat gacattttaa ataagtttat gtatacatct | 900 |
| gaatgaaaag caaagctaaa tatgtttaca gaccaaagtg tgatttcaca ctgttttaa | 960 |
| atctagcatt attcattttg cttcaatcaa aagtggtttc aatatttttt ttagttggtt | 1020 |
| agaatacttt cttcatagtc acattctctc aacctataat ttggaatatt gttgtggtct | 1080 |

```
tttgtttttt ctcttagtat agcatttta aaaaaatata aaagctacca atctttgtac      1140
aatttgtaaa tgttaagaat ttttttata tctgttaaat aaaaattatt tccaacaacc      1200
ttaatatctt taaa                                                      1214
```

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4

```
ccactggaaa cctctggagt tg                                               22
```

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5

```
aagttcacac aaaggaagcc ccgc                                             24
```

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6

```
gtgtgttttg aggtgtggtc cc                                               22
```

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7

```
tggatgtgga atgtgtgcga gg                                               22
```

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8

```
gaccccttca ttgacctcca ctac                                             24
```

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
acatactcag caccagcatc gc                                              22

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gaatgcctga gggaaatctt tgag                                            24

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cgtctccttt tgggtaatct gcg                                             23

<210> SEQ ID NO 12
<211> LENGTH: 19
<212> TYPE: PRT
<213> ORGANISM: Homo sapiens

<400> SEQUENCE: 12

Gly Asp Ala Ser Thr Gly Trp Asn Ser Val Ser Arg Ile Ile Ile Glu
1               5                   10                  15

Glu Leu Pro

<210> SEQ ID NO 13
<211> LENGTH: 16
<212> TYPE: PRT
<213> ORGANISM: Homo sapiens

<400> SEQUENCE: 13

Ser Glu Ile Pro Lys Gly Lys Gln Lys Ala Gln Leu Arg Gln Arg Glu
1               5                   10                  15

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 14

His His His His His His
1               5

METHODS FOR TREATING METABOLIC SYNDROME WITH CTHRC1 POLYPEPTIDE

RELATED APPLICATIONS

This application claims the benefit of priority under 35 U.S.C. §119(e) to U.S. Provisional Application No. 61/667,713, filed Jul. 3, 2012, which is incorporated herein by reference in its entirety.

STATEMENT OF RIGHTS TO INVENTIONS MADE UNDER FEDERALLY SPONSORED RESEARCH

This work was supported by the following grants from the from the National Center for Research Resources, Grant Nos.: HL69182 and P20 RR-15555. The government has certain rights in the invention.

SEQUENCE LISTING

The instant application contains a Sequence Listing which has been submitted electronically in ASCII format and is hereby incorporated by reference in its entirety. Said ASCII copy, created on Jul. 30, 2014, is named 90931 (307284)_SL.txt and is 8,332 bytes in size.

BACKGROUND

Metabolic syndrome is a name for a group of risk factors that occur together and increase the risk for coronary artery disease, stroke, and type 2 diabetes. Metabolic syndrome is becoming more and more common in the United States. Researchers are not sure whether the syndrome is due to one single cause, but all of the risks for the syndrome are related to obesity. The two most important risk factors for metabolic syndrome are: extra weight around the middle and upper parts of the body (central obesity), where the body may be described as "apple-shaped;" and insulin resistance, in which the body cannot use insulin effectively. Insulin is needed to help control the amount of sugar in the body. As a result, blood sugar and fat levels rise. Other risk factors include: aging. genetic propensity, hormone changes, and lack of exercise. People who have metabolic syndrome often have two other problems that can either cause the condition or make it worse: excess blood clotting and low levels of inflammation throughout the body. At present effective means for treating and preventing metabolic syndrome are needed.

SUMMARY OF INVENTION

As described below, the present invention features compositions and methods for treating and preventing a metabolic syndrome featuring the collagen triple helix repeat containing-1 (Cthrc1) protein.

Specifically, provided is a method of treating or preventing metabolic syndrome in a subject by administering an effective amount of a Collagen Triple Helix Repeat Containing 1 (Cthrc1) polypeptide or a polynucleotide encoding the polypeptide to the subject, thereby treating or preventing metabolic syndrome.

Also provided are methods of treating or preventing a metabolic syndrome associated condition selected from the group consisting of type II diabetes, hyperlipidemia, elevated triglycerides, elevated blood pressure or hypertension, hyperglycemia, and obesity by administering an effective amount of a Collagen Triple Helix Repeat Containing 1 (Cthrc1) polypeptide or a polynucleotide encoding the polypeptide to the subject, thereby treating or preventing a metabolic syndrome associated condition.

Method for reducing excess lipid and glycogen storage in a tissue or organ of a subject are carried out by administering an effective amount of a Collagen Triple Helix Repeat Containing 1 (Cthrc1) polypeptide or a polynucleotide encoding the polypeptide to the subject, thereby reducing lipid and glycogen storage in a tissue or organ of said subject.

Also provided are methods of treating or preventing steatosis in a subject by administering an effective amount of a Collagen Triple Helix Repeat Containing 1 (Cthrc1) polypeptide or a polynucleotide encoding the polypeptide to the subject, thereby treating or preventing steatosis in the subject. In some cases, the steatosis is selected from the group consisting of hepatic steatosis and cardiac steatosis.

Preferably, the composition is administered systemically.

The methods provided herein reduce the risk of heart disease or diabetes. In some cases, the effective amount of Cthrc1 is sufficient to reduce lipids in target organs by at least 40%, e.g., at least 45%, at least 50%, at least 55%, at least 60%, at least 65%, at least 70%, at least 75%, at least 80%, at least 85%, at least 90%, or at least 95%.

Optionally, the methods comprise identifying the subject as having or at risk of developing a metabolic syndrome or an associated condition.

Also provided is an antibody that specifically binds a CTHRC1 polypeptide. For example, the antibody specifically binds a conserved C terminus of Cthrc1 comprising amino acid sequence: GDASTGWNSVSRIIIEELP (SEQ ID NO:12).

The invention provides a mouse lacking Cthrc1, wherein Cthrc1 exons 2-4 are replaced with a PGK-neo cassette.

Methods for identifying a subject having a defect in lipid storage or cellular glycogen levels are carried out by determining the level of a Cthrc1 polypeptide in a biological sample from the subject, wherein a reduced level of Cthrc1 relative to a reference is indicative of the subject having a defect in lipid storage or cellular glycogen levels.

Also provided are methods of identifying a subject at risk of developing steatosis comprising determining the level of a Cthrc1 polypeptide in a biological sample from the subject, wherein a reduced level of Cthrc1 relative to a reference is indicative of an increased risk of developing steatosis.

The details of one or more embodiments of the invention are set forth in the description below. Other features, objects, and advantages of the invention will be apparent from the description and from the claims.

DEFINITIONS

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "agent" is meant any small molecule chemical compound, antibody, nucleic acid molecule, or polypeptide, or fragments thereof.

By "Collagen Triple Helix Repeat Containing 1" or "Cthrc1" is meant a polypeptide having at least about 85%, e.g., at least about 90%, at least about 95%, or at least about 99%, sequence identity to NCBI Accession No. NP_AAQ89273, or a fragment thereof that regulates metabolism. An exemplary sequence of human Cthrc1 is (SEQ ID NO: 1):

```
  1 mrpqgpaasp grlrglllll llqlpapssa seipkgkqka qlrgrevvdl yngmclqgpa
 61 gvpgrdgspg anvipgtpgi pgrdgfkgek geclresfee swtpnykqcs wsslnygidl
121 gkiaectftk mrsnsalrvl fsgslrlkcr naccqrwyft fngaecsgpl pieaiiyldq
181 gspemnstin ihrtssvegl cegigaglvd vaiwvgtcsd ypkgdastgw nsysriiiee
241 lpk
```

By a "nucleic acid encoding Cthrc1" is meant a nucleic acid having at least about 85%, e.g., at least about 90%, at least about 95%, or at least about 99%, sequence identity to NCBI Accession No. NM_138455 or NM_001256099. An exemplary nucleic acid encoding Cthrc1 is (SEQ ID NO: 2):

```
   1 gggagggaga gaggcgcgcg ggtgaaaggc gcattgatgc agcctgcggc ggcctcggag
  61 cgcggcggag ccagacgctg accacgttcc tctcctcggt ctcctccgcc tccagctccg
 121 cgctgcccgg cagccgggag ccatgcgacc ccagggcccc gccgcctccc cgcagcggct
 181 ccgcggcctc ctgctgctcc tgctgctgca gctgcccgcg ccgtcgagcg cctctgagat
 241 ccccaagggg aagcaaaagg cgcagctccg gcagagggag gtggtggacc tgtataatgg
 301 aatgtgctta caagggccag caggagtgcc tggtcgagac gggagccctg ggccaatgg
 361 cattccgggt acacctggga tcccaggtcg ggatggattc aaaggagaaa aggggaatg
 421 tctgagggaa agctttgagg agtcctggac acccaactac aagcagtgtt catggagttc
 481 attgaattat ggcatagatc ttgggaaaat tgcggagtgt acatttacaa agatgcgttc
 541 aaatagtgct ctaagagttt tgttcagtgg ctcacttcgg ctaaaatgca gaaatgcatg
 601 ctgtcagcgt tggtatttca cattcaatgg agctgaatgt tcaggacctc ttcccattga
 661 agctataatt tatttggacc aaggaagccc tgaaatgaat tcaacaatta atattcatcg
 721 cacttcttct gtggaaggac tttgtgaagg aattggtgct ggattagtgg atgttgctat
 781 ctgggttggt acttgttcag attacccaaa aggagatgct tctactggat ggaattcagt
 841 ttctcgcatc attattgaag aactaccaaa ataaatgctt taatttttcat ttgctacctc
 901 tttttttatt atgccttgga atggttcact taaatgacat tttaaataag tttatgtata
 961 catctgaatg aaaagcaaag ctaaatatgt ttacagacca aagtgtgatt tcacactgtt
1021 tttaaatcta gcattattca ttttgcttca atcaaaagtg gtttcaatat ttttttttagt
1081 tggttagaat actttcttca tagtcacatt ctctcaacct ataatttgga atattgttgt
1141 ggtcttttgt tttttctctt agtatagcat ttttaaaaaa atataaaagc taccaatctt
1201 tgtacaattt gtaaatgtta agaattttt ttatatctgt taaataaaaa ttatttccaa
1261 caaccttaat atctttaaa
```

Another exemplary nucleic acid encoding Cthrc1 is (SEQ ID NO: 3):

```
   1 agaaggttta aggccggaaa gggaaatgaa ggggcccggc gctaaccctc taaggacctg
  61 ttttgcttct gtttaaacca aatgggcagt ctgtcattac acacaccctg ggtcttcata
 121 tgtggccgcc aggtaggagc atcacagtca agctacggga gaaaacagtt tccaggaaac
 181 tggaaatgaa cggcccgagt gctttccagg ggctcatctg tgggaagtat aatggaatgt
 241 gcttacaagg gccagcagga gtgcctggtc gagacgggag ccctggggcc aatggcattc
 301 cgggtacacc tgggatccca ggtcgggatg gattcaaagg agaaaagggg gaatgtctga
```

```
-continued
 361 gggaaagctt tgaggagtcc tggacaccca actacaagca gtgttcatgg agttcattga 421 attatggcat agatcttggg aaaattgcgg agtgtacatt tacaaagatg cgttcaaata 481 gtgctctaag agttttgttc agtggctcac ttcggctaaa atgcagaaat gcatgctgtc 541 agcgttggta tttcacattc aatggagctg aatgttcagg acctcttccc attgaagcta 601 taatttattt ggaccaagga agccctgaaa tgaattcaac aattaatatt catcgcactt 661 cttctgtgga aggactttgt gaaggaattg gtgctggatt agtggatgtt gctatctggg 721 ttggtacttg ttcagattac ccaaaaggag atgcttctac tggatggaat tcagtttctc 781 gcatcattat tgaagaacta ccaaaataaa tgctttaatt ttcatttgct acctcttttt 841 ttattatgcc ttggaatggt tcacttaaat gacattttaa ataagtttat gtatacatct 901 gaatgaaaag caaagctaaa tatgtttaca gaccaaagtg tgatttcaca ctgttttaa 961 atctagcatt attcattttg cttcaatcaa aagtggtttc aatattttt ttagttggtt 1021 agaatacttt cttcatagtc acattctctc aacctataat ttggaatatt gttgtggtct 1081 tttgtttttt ctcttagtat agcatttta aaaaatata aaagctacca atctttgtac 1141 aatttgtaaa tgttaagaat tttttttata tctgttaaat aaaaattatt tccaacaacc 1201 ttaatatctt taaa
```

By "metabolic syndrome" is meant that a subject has a condition characterized by at least two of increased triglycerides, reduced HDL, increased blood pressure, increased fasting plasma glucose or type 2 diabetes, or obesity.

By "metabolic syndrome associated condition" is meant type II diabetes, hyperlipidemia, elevated triglycerides, elevated blood pressure or hypertension, hyperglycemia, and obesity.

By "control" or "reference" is meant a standard of comparison. As used herein, "changed as compared to a control" sample or subject is understood as having a level of the analyte or diagnostic or therapeutic indicator to be detected at a level that is statistically different than a sample from a normal, untreated, or control sample. Control samples include, for example, cells in culture, one or more laboratory test animals, or one or more human subjects. Methods to select and test control samples are within the ability of those in the art. An analyte can be a naturally occurring substance that is characteristically expressed or produced by the cell or organism (e.g., an antibody, a protein) or a substance produced by a reporter construct (e.g., β-galactosidase or luciferase). Depending on the method used for detection the amount and measurement of the change can vary. Determination of statistical significance is within the ability of those skilled in the art, e.g., the number of standard deviations from the mean that constitute a positive result.

As used herein, "detecting", "detection" and the like are understood that an assay performed for identification of a specific analyte in a sample, e.g., an antigen in a sample or the level of an antigen in a sample. The amount of analyte or activity detected in the sample can be none or below the level of detection of the assay or method.

By "diagnosing" and the like as used herein refers to a clinical or other assessment of the condition of a subject based on observation, testing, or circumstances for identifying a subject having a disease, disorder, or condition based on the presence of at least one indicator, such as a sign or symptom of the disease, disorder, or condition. Typically, diagnosing using the method of the invention includes the observation of the subject for multiple indicators of the disease, disorder, or condition in conjunction with the methods provided herein. A diagnostic methods provide an indicator that a disease is or is not present. A single diagnostic test typically does not provide a definitive conclusion regarding the disease state of the subject being tested.

By "effective amount" is meant the amount of a required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

The term "polynucleotide" or "nucleic acid" as used herein designates mRNA, RNA, cRNA, cDNA or DNA. As used herein, a "nucleic acid encoding a polypeptide" is understood as any possible nucleic acid that upon (transcription and) translation would result in a polypeptide of the desired sequence. The degeneracy of the nucleic acid code is well understood. Further, it is well known that various organisms have preferred codon usage, etc. Determination of a nucleic acid sequence to encode any polypeptide is well within the ability of those of skill in the art.

As used herein, "isolated" or "purified" when used in reference to a polypeptide means that a naturally polypeptide or protein has been removed from its normal physiological environment (e.g., protein isolated from plasma or tissue, optionally bound to another protein) or is synthesized in a non-natural environment (e.g., artificially synthesized in an in vitro translation system or using chemical synthesis). Thus, an "isolated" or "purified" polypeptide can be in a cell-free solution or placed in a different cellular environment (e.g., expressed in a heterologous cell type). The term "purified" does not imply that the polypeptide is the only polypeptide present, but that it is essentially free (about 90-95%, up to 99-100% pure) of cellular or organismal material naturally associated with it, and thus is distinguished from naturally occurring polypeptide. Similarly, an isolated nucleic acid is removed from its normal physiological environment. "Isolated" when used in reference to a cell means the cell is in culture (i.e., not in an animal), either cell culture or organ culture, of a primary cell or cell line. Cells can be isolated from a normal animal, a transgenic animal, an animal having spontaneously occurring genetic changes, and/or an animal having a genetic and/or induced disease or condition. An isolated virus or viral vector is a virus that is removed from the cells, typically in culture, in which the virus was produced.

As used herein, "kits" are understood to contain at least one non-standard laboratory reagent for use in the methods of the invention in appropriate packaging, optionally containing instructions for use. The kit can further include any other components required to practice the method of the invention, as dry powders, concentrated solutions, or ready to use solutions. In some embodiments, the kit comprises one or more containers that contain reagents for use in the methods of the invention; such containers can be boxes, ampules, bottles, vials, tubes, bags, pouches, blister-packs, or other suitable container forms known in the art. Such containers can be made of plastic, glass, laminated paper, metal foil, or other materials suitable for holding reagents.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 .mu.g/ml denatured salmon sperm DNA (ssDNA). In a most preferred embodiment, hybridization will occur at 42° C. C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42.degree. C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

"Obtaining" is understood herein as manufacturing, purchasing, or otherwise coming into possession of.

As used herein, "operably linked" is understood as joined, preferably by a covalent linkage, e.g., joining an amino-terminus of one peptide, e.g., expressing an enzyme, to a carboxy terminus of another peptide, e.g., expressing a signal sequence to target the protein to a specific cellular compartment; joining a promoter sequence with a protein coding sequence, in a manner that the two or more components that are operably linked either retain their original activity, or gain an activity upon joining such that the activity of the operably linked portions can be assayed and have detectable activity, e.g., enzymatic activity, protein expression activity.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, α-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical, transdermal, buccal, sublingual, intramuscular, intracardiac, intraperotineal, intrathecal, intracranial, rectal, vaginal and/or parenteral administration. The formulations may conveniently be presented in unit dosage form and may be prepared by any methods well known in the art of pharmacy. The amount of active ingredient that can be combined with a carrier material to produce a single dosage form will generally be that amount of the compound that produces a therapeutic effect.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

As used herein, "plurality" is understood to mean more than one. For example, a plurality refers to at least two, three, four, five, or more.

A "polypeptide" or "peptide" as used herein is understood as two or more independently selected natural or non-natural amino acids joined by a covalent bond (e.g., a peptide bond). A peptide can include 2, 3, 4, 5, 6, 7, 8, 9, 10, 11, 12, 13, 14, 15, 16, 17, 18, 19, 20, or more natural or non-natural amino acids joined by peptide bonds. Polypeptides as described herein include full length proteins (e.g., fully processed proteins) as well as shorter amino acids sequences (e.g., fragments of naturally occurring proteins or synthetic polypeptide fragments). Optionally the peptide further includes one or more modifications such as modified peptide bonds, i.e., peptide isosteres, and may contain amino acids other than the 20 gene-encoded amino acids. The polypeptides may be modified by either natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formulation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, Proteins, Structure and Molecular Properties, 2nd ed., T. E. Creighton, W.H. Freeman and Company, New York (1993); Posttranslational Covalent Modification of Proteins, B. C. Johnson, ed., Academic Press, New York, pgs. 1-12 (1983); Seifter et al., Meth. Enzymol 182:626-646 (1990); Rattan et al., Ann N.Y. Acad. Sci. 663:48-62 (1992)).

The term "reduce" or "increase" is meant to alter negatively or positively, respectively, by at least 5%. An alteration may be by 5%, 10%, 25%, 30%, 50%, 75%, or even by 100%.

A "sample" as used herein refers to a biological material that is isolated from its environment (e.g., blood or tissue from an animal, cells, or conditioned media from tissue culture) and is suspected of containing, or known to contain an analyte, such as a protein. A sample can also be a partially purified fraction of a tissue or bodily fluid. A reference sample can be a "normal" sample, from a donor not having the disease or condition fluid, or from a normal tissue in a subject having the disease or condition. A reference sample can also be from an untreated donor or cell culture not treated with an active agent (e.g., no treatment or administration of vehicle only). A reference sample can also be taken at a "zero time point" prior to contacting the cell or subject with the agent or therapeutic intervention to be tested or at the start of a prospective study.

A "subject" as used herein refers to an organism. In certain embodiments, the organism is an animal. In certain embodiments, the subject is a living organism. In certain embodiments, the subject is a cadaver organism. In certain preferred embodiments, the subject is a mammal, including, but not limited to, a human or non-human mammal. In certain embodiments, the subject is a domesticated mammal or a primate including a non-human primate. Examples of subjects include humans, monkeys, dogs, cats, mice, rats, cows, horses, goats, and sheep. A human subject may also be referred to as a patient.

A "subject sample" can be a sample obtained from any subject, typically a blood or serum sample, however the method contemplates the use of any body fluid or tissue from a subject. The sample may be obtained, for example, for diagnosis of a specific individual for the presence or absence of a particular disease or condition.

A subject "suffering from or suspected of suffering from" a specific disease, condition, or syndrome has a sufficient number of risk factors or presents with a sufficient number or combination of signs or symptoms of the disease, condition, or syndrome such that a competent individual would diagnose or suspect that the subject was suffering from the disease, condition, or syndrome. Methods for identification of subjects suffering from or suspected of suffering from conditions associated with diminished cardiac function is within the ability of those in the art. Subjects suffering from, and suspected of suffering from, a specific disease, condition, or syndrome are not necessarily two distinct groups.

As used herein, "susceptible to" or "prone to" or "predisposed to" a specific disease or condition and the like refers to an individual who based on genetic, environmental, health, and/or other risk factors is more likely to develop a disease or condition than the general population. An increase in likelihood of developing a disease may be an increase of about 10%, 20%, 50%, 100%, 150%, 200%, or more.

As used herein, the terms "treat," "treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Ranges provided herein are understood to be shorthand for all of the values within the range. This includes all individual sequences when a range of SEQ ID NOs: is provided. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Unless specifically stated or obvious from context, as used herein, the term "or" is understood to be inclusive.

Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference. Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

BRIEF DESCRIPTION OF THE DRAWINGS

FIG. 1A is the Cthrc1 gene targeting schematic showing replacement of exons 2-4 with a PGK-neo cassette. FIG. 1B shows the embryonic stem cell targeting with Southern blot analysis of genomic DNA from ES cell clones shows a targeted clone. FIG. 1C is a gel of RT-PCR reaction products showing a lack of Cthrc1 transcripts in tissues of adult Cthrc1 mutants.

FIG. 2A is a Western blot analysis of plasma from Cthrc1 transgenic mice (TG) and their negative wild-type littermates (WT). FIG. 2B is a photograph of Cthrc1 immunohistochemistry shows expression in adventitial cells of the remodeling renal artery following angiotensin II infusion, (FIG. 2C) dermal cells in 7 day old skin wounds, and (FIG. 2D) embryonic cartilage (E17.5). FIG. 2E shows that Cthrc1 expression is restricted to the midbrain in wild-type 129S6/SvEv mice and FIG. 2F shows that no expression is detected in the midbrain of a corresponding Cthrc1 null mouse.

FIG. 3A is a graph of cell density in livers of wild-type and Cthrc1 null mice (n=4 per group). FIGS. 3B & 3C are graphs showing the glycogen content in liver and skeletal muscle of wild-type and Cthrc1 null mice (n=4 per group). FIG. 3D is a photograph showing Oil red O stain of a liver section from a Cthrc1 null mouse shows macrovesicular and microvesicular steatosis and FIG. 3E is a photograph showing only minor lipid accumulations in a wild-type mouse. FIG. 3F is a photograph showing that lipid accumulations were also observed in the heart of Cthrc1 null mice (3 months of age) but not in hearts from wild-type mice (FIG. 3G).

(FIG. 4A) Supraoptic nucleus, (FIG. 4B) paraventricular nucleus, (FIG. 4C) Cthrc1 positive follicle in the anterior lobe of a 7 month old C57BL6/J male, (FIG. 4D) Cthrc1 expression in the anterior lobe, (E) often leading to extensive accumulations of Cthrc1, and (FIG. 4F) pre-absorption of antibody completely eliminates staining on an adjacent section. (FIG. 4O) Cthrc1 is expressed by some osteocytes (arrows) and osteoblasts in adult mouse bone. Scale bar=50 μm.

(FIG. 5B) and (FIG. 5D) are enlarged images of the boxed area shown in (FIG. 5A). Arrows indicate areas of Cthrc1 accumulation. Scale bar=50 μm

(FIG. 7A) Clearance curve of intra-arterially injected $^{125}$I-Cthrc1 into Cthrc1−/− mice. Half-life of the protein was calculated to be 146 min. (FIG. 7B) SDS-PAGE and autoradiographic analysis of plasma 30 min after $^{125}$I-Cthrc1 injection. Monomeric, dimeric and higher molecular weight forms of Cthrc1 were detectable. (FIG. 7C) $^{125}$I-Cthrc1 content in various tissues 6 h after injection.

DETAILED DESCRIPTION

Figure 1:
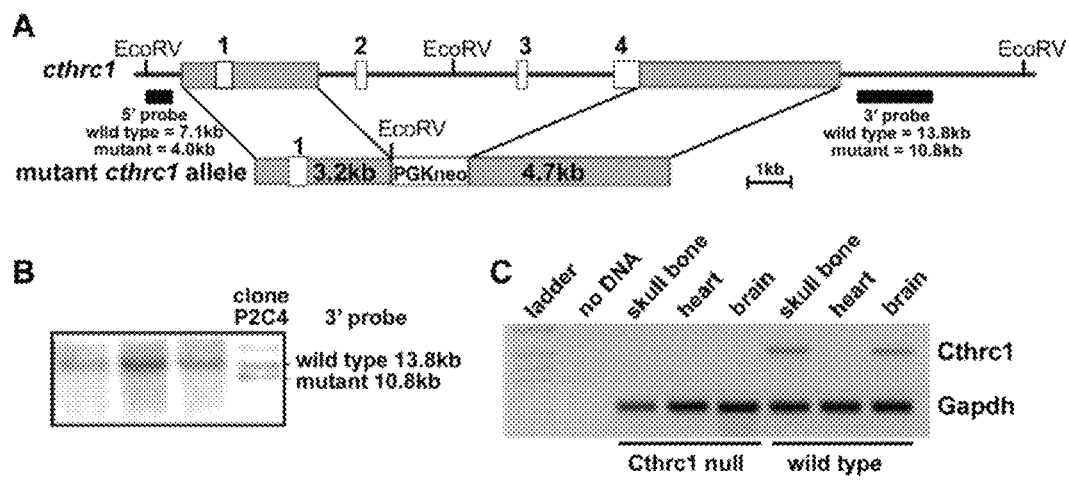
FIGS. 1A-1C are a schematic and a set of gels that show the generation of Cthrc1 null mice.

The present invention provides compositions featuring a CTHRC1 polypeptide, and fragments thereof, and methods for the use of such compositions for the treatment of metabolic syndrome or an associated condition in a subject that has or is at risk of developing metabolic syndrome.

As reported in more detail below, the present application identifies the gene Collagen Triple Helix Repeat Containing 1 (Cthrc1) and it's developmental expression and induction in adventitial cells of injured arteries and dermal cells of skin wounds. Mutant mice with a novel Cthrc1 null allele were generated by homologous recombination. Cthrc1 null mice appeared developmentally normal. On the C57BL/6J background, livers from Cthrc1 null mice accumulated vast quantities of lipid, leading to extensive macrovesicular steatosis. Glycogen levels in the liver and skeletal muscle were significantly decreased. However, Cthrc1 expression was not detectable in these tissues in wild-type mice, suggesting that the lipid and glycogen storage phenotype may be a secondary effect due to loss of Cthrc1 production at a distant site. To investigate potential hormonal functions of Cthrc1, tissues from adult mice and pigs were examined for Cthrc1 expression by immunohistochemistry with monoclonal anti-Cthrc1 antibodies. In pigs, Cthrc1 was detected around chromophobe cells of the anterior pituitary, and storage of Cthrc1 was observed in colloid-filled follicles and the pituitary cleft. Pituitary follicles have been observed in numerous vertebrates including humans but none of the known pituitary hormones have hitherto been detected in them. In C57BL/6J mice, however, Cthrc1 was predominantly expressed in the paraventricular and supraoptic nucleus of the hypothalamus but not in the posterior pituitary. In human plasma, Cthrc1 was detected in pg/ml quantities and studies with $^{125}$I-labeled Cthrc1 revealed a half-life of 2.5 hours in circulation. The highest level of Cthrc1 binding was observed in the liver. These studies identified Cthrc1 as a circulating hormone generated from the anterior pituitary, hypothalamus and bone. Hormonal functions of Cthrc1 include regulation of lipid storage and cellular glycogen levels with potentially broad implications for cell metabolism and physiology.

Accordingly, the invention provides compositions featuring a Cthrc1 polypeptide and methods of using such compositions for the treatment of metabolic syndrome, for risk factors associated with metabolic syndrome, to increase metabolism, or to reduce obesity and/or increase metabolism.
Metabolic Syndrome Metabolic syndrome is a cluster of heart disease and diabetes risk factors that occur together and increase a patient's risk for serious disease, including heart disease, stroke and diabetes. The criteria for metabolic syndrome include an increased waist circumference (abdominal obesity), elevated triglycerides, reduced high-density lipoprotein cholesterol (HDL-C), elevated blood pressure, and/or an elevated fasting glucose. In particular, levels of triglycerides of 150 mg/dL or higher; a high density lipoproteins (HDL) cholesterol lower than 40 mg/dL for men and lower than 50 mg/dL for women; a blood pressure level of 130/85 mm Hg or higher; or a fasting glucose of 100 mg/dL or higher. For most Americans, a waist circumference of 35 inches or more for women and 40 inches or more for men is considered abnormally increased. An individual who has abnormal levels of at least three of the listed criteria is considered to have metabolic syndrome. Many physicians believe that metabolic syndrome is likely associated with resistance to insulin. Metabolic syndrome increases the risk for atherosclerotic cardiovascular disease by 1.5-3 fold, and raises the risk for type 2 diabetes by 3-5 fold. It affects over 26 percent of adults, or over 50 million Americans.

Clinical management of metabolic syndrome is focused on reducing the risk for atherosclerotic cardiovascular disease, and the risk of type 2 diabetes in patients who have not yet developed clinical diabetes. Recently published results indicate that one in five adults in the U.S. has metabolic syndrome. Current methods of treating metabolic syndrome are inadequate. Compositions of the invention comprising Compositions comprising collagen triple helix repeat containing-1 (Cthrc1) are useful for the prevention or treatment of a metabolic syndrome, or for the prevention or treatment of any one or more of the risk factors associated with a metabolic syndrome.
Collagen Triple Helix Repeat Containing-1 (Cthrc1) Protein Collagen triple helix repeat containing-1 (Cthrc1) is a protein having a signal peptide which was isolated from a cDNA library of injured arteries. Cthrc1 has been reported to function as an inhibitor of TGF-β signaling. Cthrc1 is susceptible to cleavage by proteases and purified Cthrc1 forms aggregates, making it difficult to perform cell binding studies and protein interaction studies. Expression analyses of Cthrc1 in tissues have been performed by in situ hybridization, immunohistochemistry and RT-PCR analysis. Cthrc1 has also been found in plasma. Cthrc1 plasma levels in healthy human volunteers ranged from 16-440 ng/ml.

Compositions of the invention comprising an effective amount of Cthrc1 are useful for treating or preventing metabolic syndrome, or for the prevention or treatment of any one or more of the risk factors associated with a metabolic syndrome.
Polynucleotide Therapy If desired, nucleic acid molecules that encode a Cthrc1 polypeptide are delivered to a subject having or at risk of developing metabolic syndrome. The nucleic acid molecules are delivered to the cells of a subject in a form in which they can be taken up so that therapeutically effective levels of the therapeutic polypeptide or fragment thereof can be produced.

A variety of expression systems exists for the production of therapeutic polypeptides. Expression vectors useful for producing such polypeptides include, without limitation, chromosomal, episomal, and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof.

One particular bacterial expression system for polypeptide production is the *E. coli* pET expression system (e.g., pET-28) (Novagen, Inc., Madison, Wis.). According to this expression system, DNA encoding a polypeptide is inserted into a pET vector in an orientation designed to allow expression. Since the gene encoding such a polypeptide is under the control of the T7 regulatory signals, expression of the polypeptide is achieved by inducing the expression of T7

RNA polymerase in the host cell. This is typically achieved using host strains that express T7 RNA polymerase in response to IPTG induction. Once produced, recombinant polypeptide is then isolated according to standard methods known in the art, for example, those described herein.

Another bacterial expression system for polypeptide production is the pGEX expression system (Pharmacia). This system employs a GST gene fusion system that is designed for high-level expression of genes or gene fragments as fusion proteins with rapid purification and recovery of functional gene products. The protein of interest is fused to the carboxyl terminus of the glutathione S-transferase protein from *Schistosoma japonicum* and is readily purified from bacterial lysates by affinity chromatography using Glutathione Sepharose 4B. Fusion proteins can be recovered under mild conditions by elution with glutathione. Cleavage of the glutathione S-transferase domain from the fusion protein is facilitated by the presence of recognition sites for site-specific proteases upstream of this domain. For example, proteins expressed in pGEX-2T plasmids may be cleaved with thrombin; those expressed in pGEX-3X may be cleaved with factor Xa.

Alternatively, recombinant polypeptides of the invention are expressed in *Pichia pastoris*, a methylotrophic yeast. *Pichia* is capable of metabolizing methanol as the sole carbon source. The first step in the metabolism of methanol is the oxidation of methanol to formaldehyde by the enzyme, alcohol oxidase. Expression of this enzyme, which is coded for by the AOX1 gene is induced by methanol. The AOX1 promoter can be used for inducible polypeptide expression or the GAP promoter for constitutive expression of a gene of interest.

Once the recombinant polypeptide of the invention is expressed, it is isolated, for example, using affinity chromatography. In one example, an antibody (e.g., produced as described herein) raised against a polypeptide of the invention may be attached to a column and used to isolate the recombinant polypeptide. Lysis and fractionation of polypeptide-harboring cells prior to affinity chromatography may be performed by standard methods (see, e.g., Ausubel et al., supra). Alternatively, the polypeptide is isolated using a sequence tag, such as a hexahistidine tag (SEQ ID NO: 14), that binds to nickel column.

Once isolated, the recombinant protein can, if desired, be further purified, e.g., by high performance liquid chromatography (see, e.g., Fisher, Laboratory Techniques In Biochemistry and Molecular Biology, eds., Work and Burdon, Elsevier, 1980). Polypeptides of the invention, particularly short peptide fragments, can also be produced by chemical synthesis (e.g., by the methods described in Solid Phase Peptide Synthesis, 2nd ed., 1984 The Pierce Chemical Co., Rockford, Ill.). These general techniques of polypeptide expression and purification can also be used to produce and isolate useful peptide fragments or analogs (described herein).

Transducing viral (e.g., retroviral, adenoviral, and adeno-associated viral) vectors can be used for somatic cell gene therapy, especially because of their high efficiency of infection and stable integration and expression (see, e.g., Cayouette et al., Human Gene Therapy 8:423-430, 1997; Bloomer et al., Journal of Virology 71:6641-6649, 1997; Naldini et al., Science 272:263-267, 1996; and Miyoshi et al., Proc. Natl. Acad. Sci. U.S.A. 94:10319, 1997). For example, a polynucleotide encoding a stem cell recruiting factor, variant, or a fragment thereof, can be cloned into a retroviral vector and expression can be driven from its endogenous promoter, from the retroviral long terminal repeat, or from a promoter specific for a tissue or cell of interest. Other viral vectors that can be used include, for example, a vaccinia virus, a bovine papilloma virus, or a herpes virus, such as Epstein-Barr Virus (also see, for example, the vectors of Miller, Human Gene Therapy 15-14, 1990; Friedman, Science 244:1275-1281, 1989; Eglitis et al., BioTechniques 6:608-614, 1988; Tolstoshev et al., Current Opinion in Biotechnology 1:55-61, 1990; Sharp, The Lancet 337:1277-1278, 1991; Cornetta et al., Nucleic Acid Research and Molecular Biology 36:311-322, 1987; Anderson, Science 226:401-409, 1984; Moen, Blood Cells 17:407-416, 1991; Miller et al., Biotechnology 7:980-990, 1989; Le Gal La Salle et al., Science 259:988-990, 1993; and Johnson, Chest 107:77 S-83S, 1995). Retroviral vectors are particularly well developed and have been used in clinical settings (Rosenberg et al., N. Engl. J. Med 323:370, 1990; Anderson et al., U.S. Pat. No. 5,399,346).

Non-viral approaches can also be employed for the introduction of a therapeutic to a cell of a subject (e.g., a cell or tissue). For example, a nucleic acid molecule can be introduced into a cell by administering the nucleic acid in the presence of lipofection (Feigner et al., Proc. Natl. Acad. Sci. U.S.A. 84:7413, 1987; Ono et al., Neuroscience Letters 17:259, 1990; Brigham et al., Am. J. Med. Sci. 298:278, 1989; Staubinger et al., Methods in Enzymology 101:512, 1983), asialoorosomucoid-polylysine conjugation (Wu et al., Journal of Biological Chemistry 263:14621, 1988; Wu et al., Journal of Biological Chemistry 264:16985, 1989), or by micro-injection under surgical conditions (Wolff et al., Science 247:1465, 1990). Preferably the nucleic acids are administered in combination with a liposome and protamine.

Gene transfer can also be achieved using non-viral means involving transfection in vitro. Such methods include the use of calcium phosphate, DEAE dextran, electroporation, and protoplast fusion. Liposomes can also be potentially beneficial for delivery of DNA into a cell. Transplantation of normal genes into the affected tissues of a subject can also be accomplished by transferring a normal nucleic acid into a cultivatable cell type ex vivo (e.g., an autologous or heterologous primary cell or progeny thereof), after which the cell (or its descendants) are injected into a targeted tissue.

cDNA expression for use in polynucleotide therapy methods can be directed from any suitable promoter (e.g., the human cytomegalovirus (CMV), simian virus 40 (SV40), or metallothionein promoters), and regulated by any appropriate mammalian regulatory element. Exemplary constitutive promoters include the promoters for the following genes which encode certain constitutive or "housekeeping" functions: hypoxanthine phosphoribosyl transferase (HPRT), dihydrofolate reductase (DHFR) (Scharfmann et al., *Proc. Natl. Acad. Sci. USA* 88:4626-4630 (1991)), adenosine deaminase, phosphoglycerol kinase (PGK), pyruvate kinase, phosphoglycerol mutase, the actin promoter (Lai et al., *Proc. Natl. Acad. Sci. USA* 86: 10006-10010 (1989)), and other constitutive promoters known to those of skill in the art. In addition, many viral promoters function constitutively in eukaryotic cells. These include: the early and late promoters of SV40; the long terminal repeats (LTR) of Moloney Leukemia Virus and other retroviruses; and the thymidine kinase promoter of Herpes Simplex Virus, among many others. Accordingly, any of the above-referenced constitutive promoters can be used to control transcription of a heterologous gene insert.

Genes that are under the control of inducible promoters are expressed only or to a greater degree, in the presence of an inducing agent, (e.g., transcription under control of the metallothionein promoter is greatly increased in presence of certain metal ions). Inducible promoters include responsive elements (REs) which stimulate transcription when their inducing factors are bound. For example, there are REs for serum factors, steroid hormones, retinoic acid and cyclic AMP. Promoters containing a particular RE can be chosen in order to obtain an inducible response and in some cases, the RE itself may be attached to a different promoter, thereby conferring inducibility to the recombinant gene. Thus, by selecting the appropriate promoter (constitutive versus inducible; strong versus weak), it is possible to control both the existence and level of expression of a therapeutic agent in the genetically modified stem cell and/or in a cell of the tissue having a deficiency in cell number. Selection and optimization of these factors for delivery of a therapeutically effective dose of a particular therapeutic agent is deemed to be within the scope of one of ordinary skill in the art without undue experimentation, taking into account the above-disclosed factors and the clinical profile of the subject.

In addition to at least one promoter and at least one heterologous nucleic acid encoding the therapeutic agent, the expression vector preferably includes a selection gene, for example, a neomycin resistance gene, for facilitating selection of stem cells that have been transfected or transduced with the expression vector.

If desired, enhancers known to preferentially direct gene expression in specific cell types can be used to direct the expression of a nucleic acid. The enhancers used can include, without limitation, those that are characterized as tissue- or cell-specific enhancers. Alternatively, if a genomic clone is used as a therapeutic construct, regulation can be mediated by the cognate regulatory sequences or, if desired, by regulatory sequences derived from a heterologous source, including any of the promoters or regulatory elements described above.

Another therapeutic approach included in the invention involves administration of a recombinant therapeutic, such as a recombinant stem cell recruiting factor, variant, or fragment thereof, either directly to the site of a potential or actual disease-affected tissue or systemically (for example, by any conventional recombinant protein administration technique). The dosage of the administered protein depends on a number of factors, including the size and health of the individual subject. For any particular subject, the specific dosage regimes should be adjusted over time according to the individual need and the professional judgment of the person administering or supervising the administration of the compositions.

Pharmaceutical Compositions and Administration

The present invention contemplates pharmaceutical preparations comprising a human Cthrc1 polypeptide together with a pharmaceutically acceptable carrier. Such compositions are useful for the treatment or prevention of metabolic syndrome, or for the prevention or treatment of any one or more of the risk factors associated with a metabolic syndrome. Polypeptides of the invention may be administered as part of a pharmaceutical composition. The compositions should be sterile and contain a therapeutically effective amount of the polypeptides in a unit of weight or volume suitable for administration to a subject.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups also can be derived from inorganic bases such as, for example, sodium, potassium, ammonium, calcium or ferric hydroxides, and such organic bases as isopropylamine, trimethyl amine, 2-ethylamino ethanol, histidine, procaine and the like. Particularly preferred are the salts of TFA and HCl.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes.

Liquid compositions also can contain liquid phases in addition to and to the exclusion of water. Exemplary of such additional liquid phases are glycerin, vegetable oils such as cottonseed oil, and water-oil emulsions.

A therapeutic composition contains an inflammation inhibiting amount or a fibrosis inhibiting amount of an Cthrc1 polypeptide of the present invention, typically formulated to contain an amount of at least 0.1 weight percent of Cthrc1 polypeptide per weight of total therapeutic composition. A weight percent is a ratio by weight of inhibitor to total composition. Thus, for example, 0.1 weight percent is 0.1 grams of inhibitor per 100 grams of total composition.

These compositions can be stored in unit or multi-dose containers, for example, sealed ampoules or vials, as an aqueous solution or as a lyophilized formulation for reconstitution. As an example of a lyophilized formulation, 10 mL vials are filled with 5 mL of sterile-filtered 1% (w/v) aqueous Cthrc1 polypeptide solution, and the resulting mixture can then be lyophilized. The infusion solution can be prepared by reconstituting the lyophilized material using sterile Water-for-Injection (WFI).

The compositions can be administered in effective amounts. The effective amount will depend upon the mode of administration, the particular condition being treated, and the desired outcome. It may also depend upon the stage of the condition, the age and physical condition of the subject, the nature of concurrent therapy, if any, and like factors well known to the medical practitioner. For therapeutic applications, it is that amount sufficient to achieve a medically desirable result.

The dosage ranges for the administration of the Cthrc1 polypeptide vary. In general, amounts are large enough to produce the desired effect in which disease symptoms of a metabolic syndrome are ameliorated. The dosage should not be so large as to cause adverse side effects. Generally, the dosage will vary with the age, condition, sex and extent of the disease in the patient and can be determined by one of skill in the art. The dosage also can be adjusted by the individual physician in the event of any complication.

A therapeutically effective amount is an amount of Cthrc1 sufficient to produce a measurable inhibition of symptoms of a metabolic syndrome (e.g., an increase in metabolic rate or a decrease in obesity). Such symptoms are measured in conjunction with assessment of related clinical parameters.

A therapeutically effective amount of a Cthrc1 polypeptide of this invention in the form of a polypeptide, or fragment thereof, is typically an amount of polypeptide such that when administered in a physiologically tolerable composition is sufficient to achieve a plasma concentration of from about 0.1 microgram (ug) per milliliter (mL) to about 200 ug/mL, or from about 1 ug/mL to about 150 ug/mL. In one embodiment, the plasma concentration in molarity is from about 2 micromolar (uM) to about 5 millimolar (mM) or from 100 uM to 1 mM Cthrc1 polypeptide. In other embodiments, the doses of polypeptide ranges from about 500 mg/Kg to about 1.0 g/kg (e.g., 500, 600, 700, 750, 800, 900, 1000 mg/kg).

The agents of the invention can be administered parenterally by injection or by gradual infusion over time. In other embodiments, agents are administered intravenously, intraperitoneally, intramuscularly, subcutaneously, intracavity, transdermally, topically, intraocularly, orally, intranasally, and can be delivered by peristaltic means. In one embodiment, a therapeutic compositions containing an agent of this invention are administered in a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered and timing depends on the patient to be treated, capacity of the patient's system to utilize the active ingredient, and degree of therapeutic effect desired. Precise amounts of active ingredient required to be administered depend on the judgement of the practitioner and are peculiar to each individual. However, suitable dosage ranges for systemic application are disclosed herein and depend on the route of administration. Suitable regimes for administration also are variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

Cthrc1 can be administered as a peptide, either modified or unmodified, for example to modify the pharmacokinetic and/or pharmacodynamic properties of the peptide. A Cthrc1 peptide can be administered as a full-length peptide, or as a peptide not including the signal sequence (corresponding to amino acids 1 to 30 of the sequence). The peptide can be delivered as any of the peptide fragments taught in U.S. Pat. No. 6,630,325 or any of U.S. patent application Ser. Nos. 09/692,081, 10/045,992, and 10/939,233. Cthrc1 can form a multimer. Cthrc1 can be administered as a dimer, trimer, etc. Methods of expressing proteins such that they form dimeric and trimeric structures (i.e., take on their native conformations) is well known in the art.

The amount and frequency of administration of Cthrc1 would depend on a number of factors including, but not limited to, the condition to be treated. As demonstrated herein, both increasing Cthrc1 expression above normal levels and eliminating Cthrc1 expression has detrimental effects on subjects. For example, a subject could be administered a bolus of Cthrc1 or in a subject found to have chronically low levels of Cthrc1, Cthrc1 could be administered to return the subject to a normal level of Cthrc1.

Therapy

As demonstrated herein, increased levels of Cthrc1 are useful for the treatment or prevention of metabolic syndrome and associated risk factors. Subjects suffering, suspected of suffering, or prone to metabolic syndrome can be tested and monitored for expression levels of Cthrc1. Determining Cthrc1 levels can be performed at a single time point, or Cthrc1 levels can be monitored over time, as are many diagnostic markers, and substantial changes in Cthrc1 levels can be an indication that further testing for a metabolic disorder should be performed. Testing can be done using any assay specific for Cthrc1, for example any immunoassay, preferably an assay that is amenable to high throughput and/or automated screening methods. Antibodies to various portions of Cthrc1 can be generated using routine methods. Methods of epitope selection, antigen preparation, and antibody production are well known to those of skill in the art.

Therapy employing a Cthrc1 polypeptide or a polynucleotide encoding a Cthrc1 polypeptide is also provided by the invention. Therapy may be provided wherever therapy for metabolic syndromes is performed: at home, the doctor's office, a clinic, a hospital's outpatient department, or a hospital. Treatment generally begins at a hospital so that the doctor can observe the therapy's effects closely and make any adjustments that are needed. The duration of the therapy depends on the kind of cancer being treated, the age and condition of the patient, the stage and type of the patient's disease, and how the patient's body responds to the treatment. Drug administration may be performed at different intervals (e.g., daily, weekly, or monthly). Therapy may be given in on-and-off cycles that include rest periods so that the patient's body has a chance to build healthy new cells and regain its strength.

A Cthrc1 polypeptide or a polynucleotide encoding a Cthrc1 polypeptide may be administered within a pharmaceutically-acceptable diluent, carrier, or excipient, in unit dosage form. Conventional pharmaceutical practice may be employed to provide suitable formulations or compositions to administer the compounds to patients suffering from a disease that is associated with a metabolic syndrome. Administration may begin before the patient is symptomatic. Any appropriate route of administration may be employed, for example, administration may be topical, parenteral, intravenous, intraarterial, subcutaneous, intratumoral, intramuscular, intracranial, intraorbital, ophthalmic, intraventricular, intrahepatic, intracapsular, intrathecal, intracisternal, intraperitoneal, intranasal, aerosol, suppository, or oral administration. For example, therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found, for example, in "Remington: The Science and Practice of Pharmacy" Ed. A. R. Gennaro, Lippincourt Williams & Wilkins, Philadelphia, Pa., 2000. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for Cthrc1 modulatory compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

The formulations can be administered to human patients in therapeutically effective amounts (e.g., amounts which prevent, eliminate, or reduce a pathological condition) to provide therapy for a disease or condition. "Therapeutically effective amount" is intended to include an amount of a compound useful in the present invention or an amount of the combination of compounds claimed, e.g., to treat or prevent the disease or disorder, or to treat the symptoms of the disease or disorder, in a host. The combination of compounds is preferably a synergistic combination. Synergy, as described for example by Chou and Talalay, Adv. Enzyme Regul. 22:27-55 (1984), occurs when the effect of the compounds when administered in combination is greater than the additive effect of the compounds when administered alone as a single agent. In general, a synergistic effect is advantageously demonstrated at suboptimal concentrations of the compounds. Synergy can be in terms of lower cytotoxicity, increased activity, or some other beneficial effect of the combination compared with the individual components. The preferred dosage of a Cthrc1 polypeptide or a polynucleotide encoding a Cthrc1 polypeptide is likely to depend on such variables as the type and extent of the disorder, the overall health status of the particular patient, the formulation of the compound excipients, and its route of administration. If desired, treatment with an agent of the invention may be combined with therapies for the treatment of a metabolic syndrome.

For any of the methods of application described above, an agent of the invention of the invention is desirably administered intravenously or is applied to the site of a metabolic syndrome (e.g., by injection).

Kits

The invention provides kits for the treatment or prevention of a metabolic syndrome. In one embodiment, the kit includes a therapeutic or prophylactic composition containing an effective amount of an agent described herein, such as an inhibitory nucleic acid to Cthrc1 in unit dosage form. In some embodiments, the kit comprises a sterile container that contains a therapeutic or prophylactic composition; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments.

If desired an agent of the invention is provided together with instructions for administering the agent to a subject having or at risk of developing a metabolic syndrome. The instructions will generally include information about the use of the composition for the treatment or prevention of a metabolic syndrome. In other embodiments, the instructions include at least one of the following: description of the therapeutic agent; dosage schedule and administration for treatment or prevention of a metabolic syndrome or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

This invention is further illustrated by the following examples, which should not be construed as limiting. All documents mentioned herein are incorporated herein by reference.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1

Generation of Cthrc1 Null Mice

To characterize Cthrc1 function in vivo, a novel Cthrc1 null allele was generated by replacing three of the four exons (exons 2-4) with a neomycin cassette (Cthrcr1$^{tm1Vli}$) (FIG. 1A). This mutant allele resulted in a complete null with no detectable expression of Cthrc1 as determined by RT-PCR, Western blotting and immunohistochemistry (FIG. 1C, 2F). Mice carrying this allele were backcrossed more than eleven generations to obtain the mutant allele on a pure 129S6/SvEv or C57BL6/J genetic background, respectively. Cthrc1−/− mice were viable and revealed no obvious developmental abnormalities.

Example 2

Figure 2:
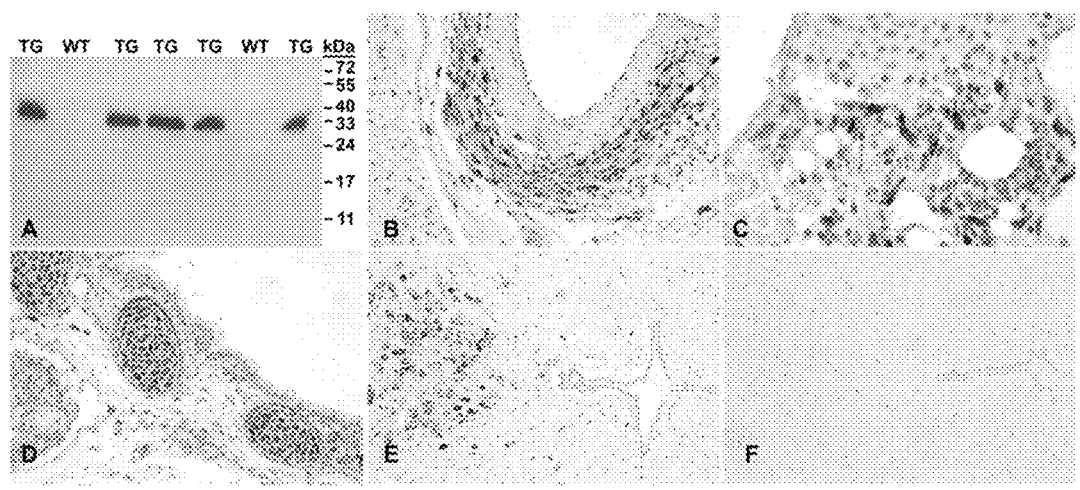
FIGS. 2A-2F are a gel and a set of photographs showing the characterization of rabbit monoclonal anti-Cthrc1 (Vli-55) antibody.
Figure 3:
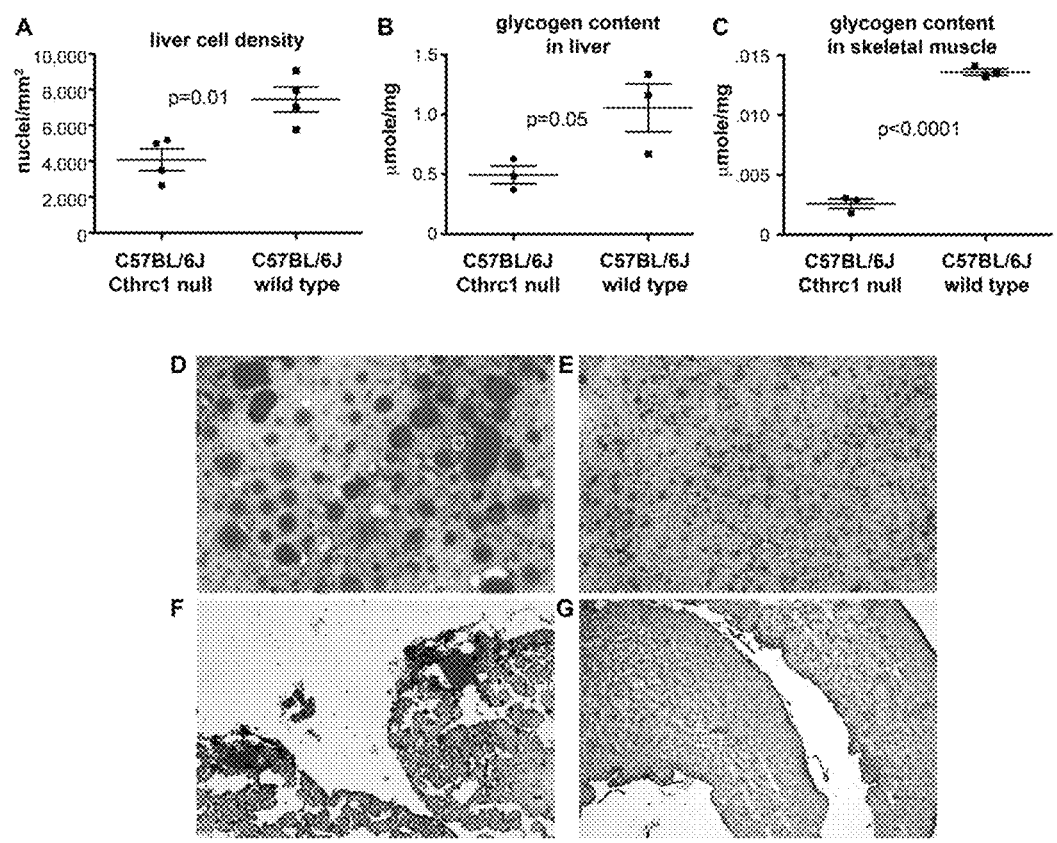
FIGS. 3A-3G are graphs and photographs that show the fatty liver and cardiac steatosis in Cthrc1 null mice.

Adult Cthrc1 Null Mice have Dramatically Increased Levels of Lipid in Their Livers and Hearts Routine histology of livers from six month old Cthrc1 null mice on the C57BL/6J background revealed strikingly larger hepatocytes compared to wild-type controls. Overall this resulted in a significantly lower cell density (FIG. 3A). Oil red O staining was performed to determine whether lipid content was increased in livers from mutants and this revealed dramatically increased lipid storage in Cthrc1 null mice resulting in macro- and micro-vesicular steatosis (FIG. 3D, E). Lipid accumulations were also observed in hearts from Cthrc1 null mice but not wild-type controls (FIG. 3F, G). Next glycogen levels in liver samples were measured. A significant decrease in glycogen in livers was present in the mutant mice (FIG. 3B). Also, a significant decrease in glycogen content was also found in skeletal muscle from mutant mice compared to wild-type controls (FIG. 3C). The abnormalities observed in liver and skeletal muscle raised the question whether Cthrc1 was expressed in these organs. A highly sensitive and specific rabbit monoclonal antibodies against the conserved C terminus of Cthrc1 were developed that allowed for the detection of Cthrc1 by western blot and in formalin fixed, paraffin embedded tissue sections by immunohistochemistry (FIG. 2). No detectable Cthrc1 was found in normal adult livers and skeletal muscle with these methods and this led to the consideration whether Cthrc1 may be a circulating factor acting as a hormone.

Example 3

Cthrc1 is Expressed in the Central Nervous System and Pituitary Gland

A comprehensive immunoblot-based and immunohistochemistry-based survey of Cthrc1 expression was undertaken in tissues from adult mice, rats and pigs. Expression of Cthrc1 in two month old C57BL/6J mice was detected in the supraoptic nucleus (SO, FIG. 4A) and paraventricular nucleus (PVH, FIG. 4B) of the hypothalamus, both of which contain neurosecretory cells with axon terminals in the posterior pituitary. Serial sectioning of the entire midbrain region, however, did not indicate that any of Cthrc1 immunoreactivity of the hypothalamus was transported to the posterior pituitary for secretion (data not shown). Cthrc1 expression was not detected anywhere in the pituitary of mice at this age nor were colloid-filled follicles found in the anterior pituitary in mice at two months of age. Similarly, neurons of the supraoptic nucleus in pigs also expressed Cthrc1 but no Cthrc1 was found in the posterior pituitary (data not shown).

Figure 4:
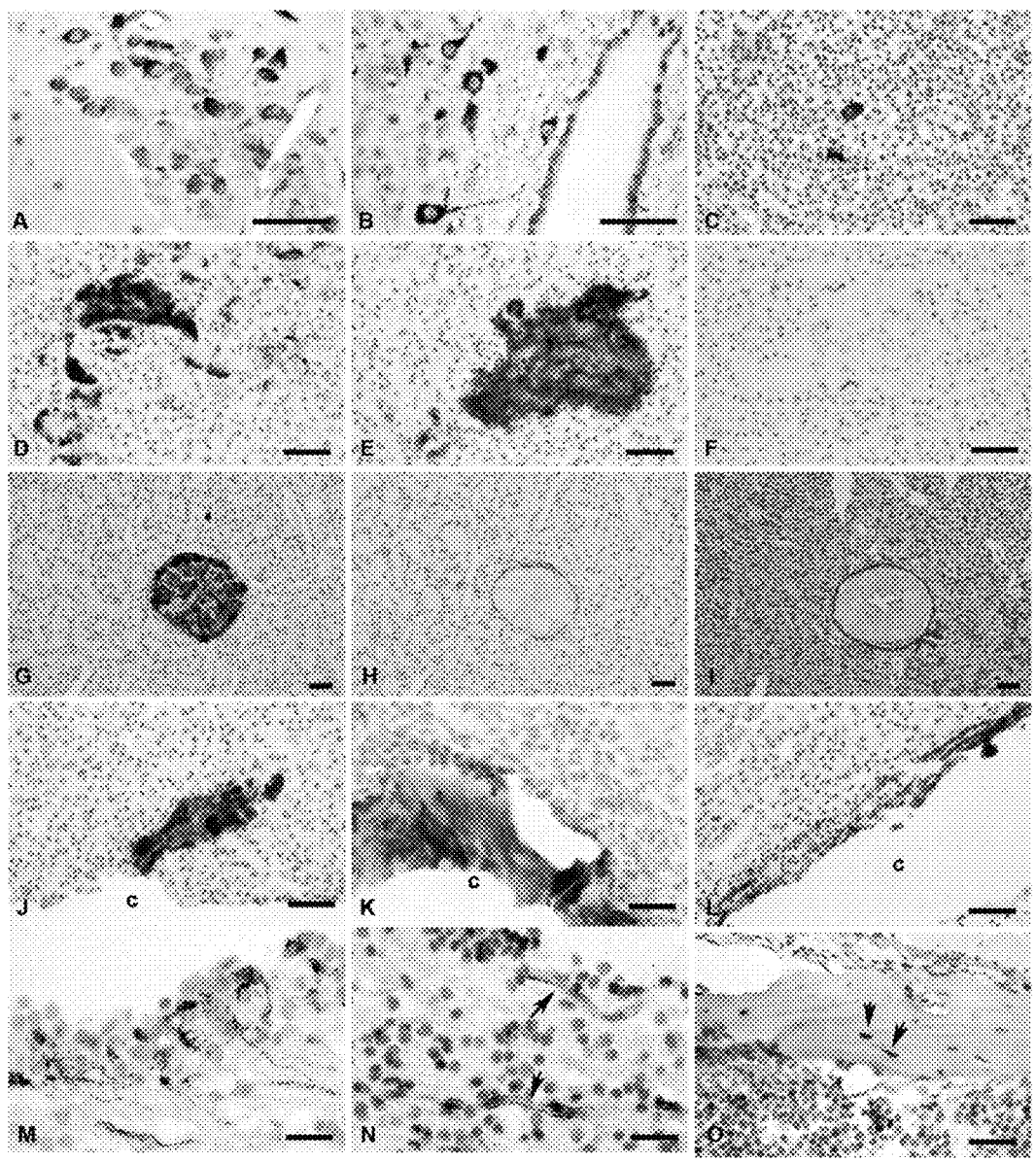
FIGS. 4A-4O are photographs showing Cthrc1 immunohistochemistry of the brain and pituitary gland from mouse and pig. Sections of mouse (FIGS. 4A-4C) and pig (FIGS. 4D-4N) brain and pituitary were immunostained for Cthrc1 expression.
(FIGS. 4G-4I) are serial sections of a typical colloid-filled follicle of the anterior pituitary with (FIG. 4G) showing extensive immunoreactivity, (FIG. 4H) which is completely eliminated by pre-absorbing the antibody with peptide antigen (FIG. 4H), (FIG. 4I) H&E stain of the follicle shows encapsulation of the follicle by folliculostellate cells.
(FIGS. 4J & 4K) Cthrc1 localization in the pituitary cleft (c) and (FIG. 4L) canaliculi connecting to the cleft.
(FIG. 4M) An isolated area of cells in the paraventricular zone of the lateral ventricle expresses Cthrc1 (note granular appearance), and (FIG. 4N) nearby small vessels (arrows) contain Cthrc1.

In wild-type mice older than six months of age, small accumulations of Cthrc1 immunoreactivity were occasionally observed in the anterior pituitary (FIG. 4C). In all pig pituitaries examined, Cthrc1 immunoreactivity was variable in extent, but was consistently localized in the anterior lobe (FIG. 4D-F). Some of the Cthrc1 was found inside the cytoplasm of cells suggesting synthesis by those cells (FIG. 4D). Often Cthrc1 was observed in the lumen of colloid-filled follicles that were lined by folliculostellate cells (FIG. 4G-I). Preincubation of the antibody with the peptide antigen completely abolished the immunoreactivity, demonstrating specificity of the antibody (FIG. 4F, H). Colloid-filled follicles of the anterior pituitary, increasing in number and size with age, have been reported in numerous vertebrates including humans (Ogawa S, et al., Arch Histol Cytol 59: 467-478; and Kameda Y, Cell Tissue Res 263: 115-124). Colloid material has also been reported in the pituitary cleft with adenohypophysial canaliculi connecting to it (Ciocca D R and Gonzalez C B, Tissue Cell 10: 725-733). Cthrc1 accumulations were found close to the cleft (FIG. 4J) and also inside the pituitary cleft (FIG. 4K), often with small canaliculi carrying Cthrc1 connecting to the cleft (FIG. 4L). The significance of pituitary colloid follicles has yet to be determined, as none of the known pituitary hormones have been localized to them. Here it was demonstrated that these follicles store Cthrc1.

As shown above, certain areas of the brain constitutively express Cthrc1. In brains from pigs, foci of paraventricular cells of the lateral ventricles were found that expressed Cthrc1 (FIG. 4M) and these sites are known to harbor neuronal stem cells. Close to the Cthrc1 expressing paraventricular cells Cthrc1 immunoreactivity was observed inside the lumen of small vessels (FIG. 4N), which provides indirect evidence that Cthrc1 is secreted into the circulation. In young animals many tissues are still growing and undergoing remodeling, including the skeletal system, which constantly remodels. Cthrc1 expression was found in some osteocytes and osteoblasts (FIG. 4O) raising the possibility that Cthrc1 derived from bone may contribute to hormonal effects on liver and muscle.

Example 4

Pharmacokinetic Properties of Cthrc1

Figure 7:
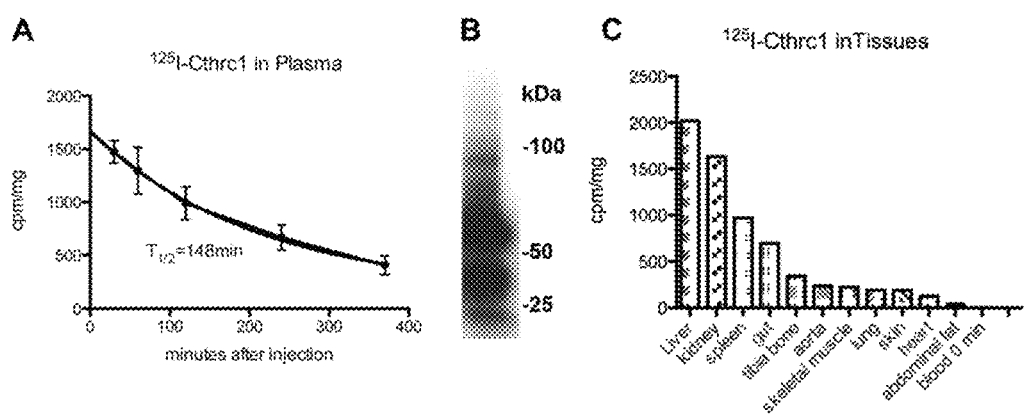
FIGS. 7A-7C are graphs and a gel that show the pharmacokinetic properties of Cthrc1.

Immunoblotting of plasma from Cthrc1 transgenic mice (Pyagay P, et al., Circ Res 96: 261-268) revealed that the pharmacokinetic properties of Chtrcl are compatible with a role of a circulating factor (FIG. 2A). To determine the half-life of Cthrc1 in circulation, $^{125}$I-labeled Cthrc1 was injected into the carotid artery of Cthrc1−/− mice and the clearance curve shown in FIG. 7A was obtained. The half-life was calculated to be 146 minutes. The integrity of the injected radiolabeled Cthrc1 after 30 minutes in circulation was examined by subjecting plasma to SDS-PAGE under non-reducing conditions followed by autoradiography. Apparent monomeric and dimeric forms of the protein were dominant with higher molecular weight oligomers also detectable (FIG. 7B). Six hours after the Cthrc1 injection the amount of Cthrc1 bound in various organs was determined. Per mg tissue the highest levels of bound Cthrc1 were found in the liver (FIG. 7C).

Example 5

Cthrc1 in Human Plasma

Figure 8:
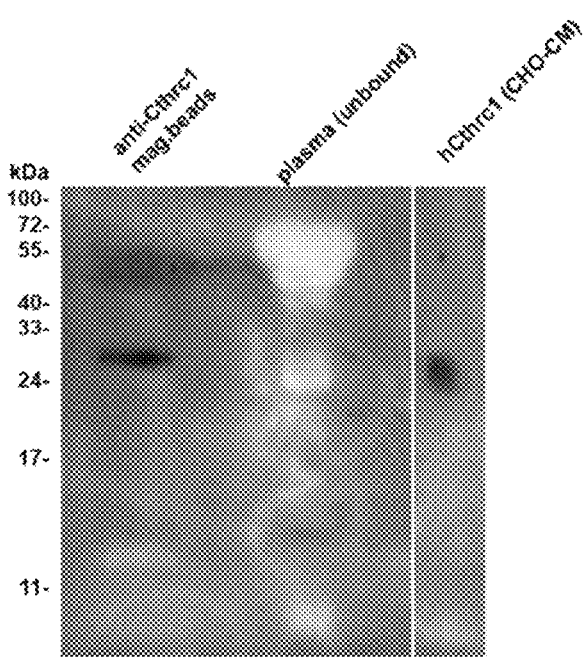
FIG. 8 is a gel that shows Cthrc1 detection in human plasma. A pull-down assay with monoclonal Cthrc1 antibody coupled to magnetic beads was performed on human plasma. The eluate was analyzed by Western blotting with HRP-conjugated anti-Cthrc1 antibody, conditioned medium from hCthrc1 expressing CHO-K1 cells was used as a positive control. No Cthrc1 was detectable in the unbound plasma fraction (not absence of non-specific bands).

Mouse monoclonal antibodies suitable for detection of Cthrc1 by ELISA were generated. These antibodies conjugated to magnetic beads were used to isolate Cthrc1 from 10 ml of plasma. The eluate from the beads was examined for the presence of Cthrc1 by Western blotting with HRP-conjugated anti-Cthrc1 antibodies showing a single band of Cthrc1 with a similar molecular mass as Cthrc1 expressed in CHO-K1 cells (FIG. 8).

Cthrc1 was identified in a screen for genes upregulated in balloon-injured arteries, where it was highly induced in activated adventitial cells. Database searches and sequence alignments revealed that Cthrc1 is a highly conserved and unique gene in chordates with no homologues found in lower species such as flies or worms (Pyagay P, et al., Circ Res 96: 261-268). With adiponectin and other members of the C1q/TNF-related protein (CTRP) family Cthrc1 shares the presence of a short N terminal collagen domain but it lacks the characteristic C1q domain that defines the CTRP family of proteins (Wong G W, et al., FASEB J 23: 241-258). Cthrc1 and adiponectin are similar in molecular mass, 243 and 244 amino acids, respectively. Like adiponectin, as described herein, Cthrc1 is a circulating hormone that forms high molecular weight complexes (Lara-Castro C et al., Diabetes 55: 249-259; and Hada Y, et al., Biochem Biophys Res Commun 356: 487-493), although the significance of the different Cthrc1 molecular weight complexes needs to be determined.

Figure 9:
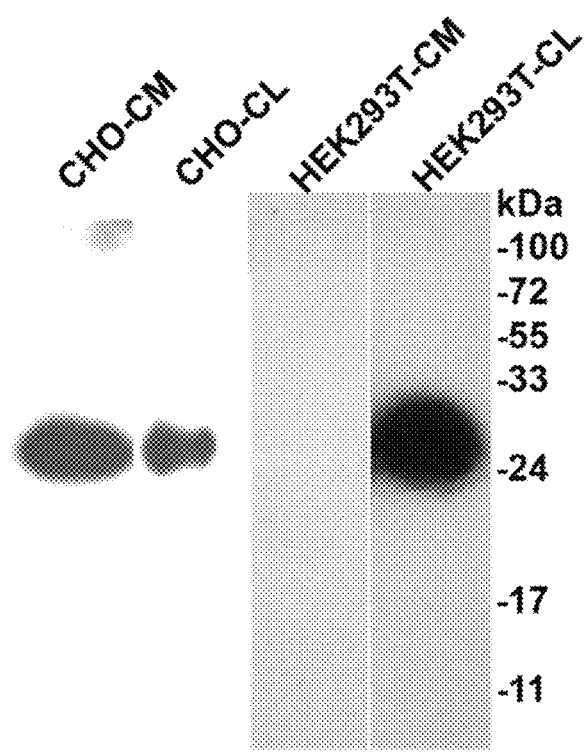
FIG. 9 is a gel that shows that Cthrc1 secretion is cell type dependent. Detection of Cthrc1 in conditioned medium (CM) and cell lysate (CL) of CHO-K1 or HEK293T cells 72 h after transfection with a Cthrc1 expression vector. Note the absence of Cthrc1 in the CM of HEK293T cells.

Yamamoto et al. (Yamamoto S, et al., Dev Cell 15: 23-36) reported an interaction of Cthrc1 with the planar cell polarity pathway (PCP) of non-canonical WNT signaling. The authors' reasoning for investigating an involvement of Cthrc1 in the PCP pathway was based on the fact that the Cthrc1 gene is located adjacent to the Frizzled6 gene, which is a WNT binding receptor. The targeted replacement of the first exon of the Cthrc1 gene by a LacZ reporter gene in mice was reported to demonstrate expression of Cthrc1 in inner ear hair cells (Yamamoto S, et al., Dev Cell 15: 23-36). Abnormalities in inner ear development occurred when Cthrc1 null mice were crossed with mice carrying one mutant allele of Vangl2, but these abnormalities were only observed when these compound mutants were on a specific mixed genetic background and not when the mutants were crossed with outbred mice (Yamamoto S, et al., Dev Cell 15: 23-36). With the antibodies described herein Cthrc1 expression in inner ear hair cells has not been detected and auditory testing did not reveal any hearing abnormalities in our mutant mice (data not shown). The use of LacZ expression as a surrogate for endogenous Cthrc1 localization has obvious limitations when the endogenous protein is released into the circulation. Yamamoto et al. (Yamamoto S, et al., Dev Cell 15: 23-36) performed most of their Cthrc1 protein interaction studies in HEK293T cells. Unlike Cthrc1 transfected CHO-K1 cells, which secrete Cthrc1 readily into the medium, Cthrc1 cannot be detected in the medium of transfected HEK293T cells (FIG. 9). Detection of Cthrc1 in plasma implies that it is secreted from cells. In the neurosecretory nuclei of the hypothalamus (FIG. 4A, B) and the paraventricular cells shown in FIG. 4M, immunoreactivity with granular appearance restricted to the cytoplasm and axon of the cell was observed.

Without being bound by theory, this is indicative of Cthrc1 packaging in secretory granules, a characteristic of a regulated release mechanism that has been described for the release of neuropeptides from neuroendocrine cells (Park J J, et al., J Mol Neurosci 37: 151-159). A role for carboxypeptidase E (CPE) in the transport of peptide hormone-containing vesicles to the site of release has been demonstrated in this process (Park J J, et al., Mol Endocrinol 22: 989-1005). An interaction of Cthrc1 with CPE still needs to be demonstrated. The presence of a C terminal lysine residue in the Cthrc1 sequence would be compatible with an interaction with CPE. The entire midbrain region with the attached pituitary was examined by serial sectioning and Cthrc1 immunohistochemistry both in mice and pigs but this analysis failed to identify evidence for transport of Cthrc1 expressed in the hypothalamus along axons to the pituitary gland. CPE also cleaves off C terminal lysine or arginine residues and if this is the case for Cthrc1, it could affect the ability of the C terminal specific antibody (Vli-55) to detect Cthrc1 by immunohistochemistry. Finding Cthrc1 in small vessels near sites of Cthrc1 expression (FIG. 4N) provides indirect evidence for the release of Cthrc1 into the circulation.

A novel Cthrc1 null mutant mouse was generated and the phenotype of the adult mutant mice was characterized. Unlike the two other reported targeted Cthrc1 mutants (Yamamoto S, et al., Dev Cell 15: 23-36; and Kimura H, et al., PLoS ONE 3: e3174), in the mutant mice described herein 3 of the 4 exons were replaced with a neomycin cassette and the lack of Cthrc1 mRNA expression was verified. Using both N terminal and C terminal specific antibodies no Cthrc1 protein was detectable, ruling out the possibility of a hypomorph phenotype. In agreement with the published Cthrc1 null mutants, the Cthrc1 null mice described herein were also viable and showed no obvious developmental abnormalities.

While Cthrc1 expression was not detectable in the liver, skeletal muscle, or heart of the wild-type mice, examination of these organs in the Cthrc1 mutant mice revealed excessively lipid storage in livers and hearts as well as reduced glycogen levels in skeletal muscle. Cardiac lipid accumulation has been identified as a major cause of cardiac dysfunction associated with diabetes and obesity (Rodrigues B, et al., Mol Cell Biochem 180: 53-57; Rodrigues B, et al., J Mol Cell Cardiol 27: 169-179; McGavock J M, et al., Ann Intern Med 144: 517-524; Atkinson L L, et al., Am J Physiol Endocrinol Metab 284: E923-930; and Christoffersen C, et al., Endocrinology 144: 3483-3490). This ultimately led to the consideration of the possibility that Cthrc1 functions as a hormone. Without wishing to be bound by theory, the data presented here indicate that hepatocytes and myocytes in vivo may express a receptor for Cthrc1 and the binding of $^{125}$I-Cthrc1 to the liver supports this concept.

With a sensitive monoclonal anti-Cthrc1 antibody suitable for detection by ELISA the presence of Cthrc1 in plasma was demonstrated. Working with plasma allowed for the deliberate avoidance of the use of secondary anti-IgG antibodies because even minimal cross-reactivity with human immunoglobulins could make discrimination between Cthrc1 and the similarly migrating band of the immunoglobulin light chain difficult on a Western blot. As shown in FIG. 2A and FIG. 8, no non-specific bands are detected with HRP-conjugated monoclonal anti-Cthrc1 antibodies in plasma samples by Western blotting. Detection of Cthrc1 in plasma of Cthrc1 transgenic mice and a half-life of approximately 2.5 hours in circulation provide additional support for Cthrc1 as a circulating factor. In the absence of a quantitative assay, the Cthrc1 levels detected in the plasma sample were estimated. Based on experience with the antibodies and the levels of Cthrc1 expressed by transduced CHO-K1 cells the levels of Cthrc1 in the plasma sample analyzed here were estimated to be below 100 pg/ml, which would be several orders of magnitude lower than those of adiponectin (typically several µg/ml) (Lihn A S, et al., Obes Rev 6: 13-21).

Figure 5:
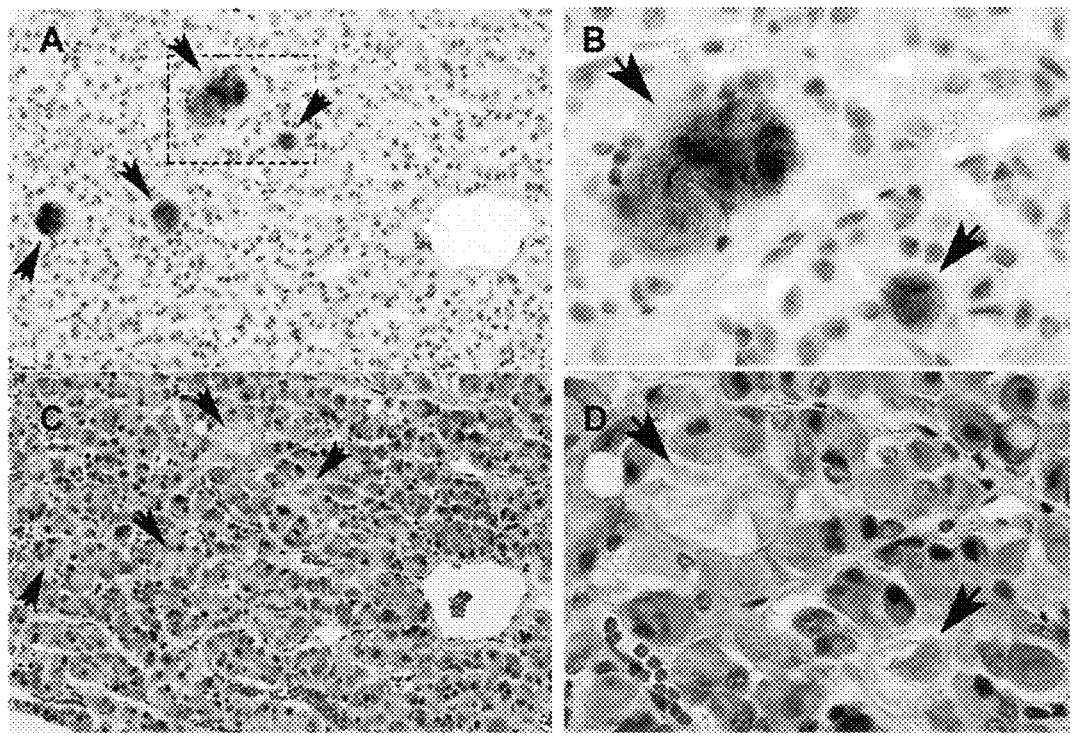
FIGS. 5A-5D are photographs showing Cthrc1 accumulation in areas surrounded by chromophobe cells of the anterior pig pituitary. Adjacent sections were stained for Cthrc1 (FIG. 5A) and morphology (FIG. 5C, H&E).
Figure 6:
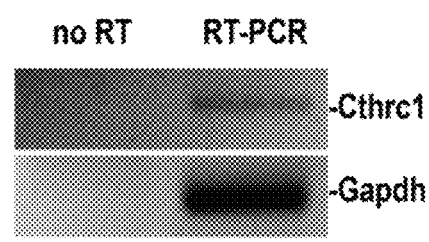
FIG. 6 is a gel that shows Cthrc1 expression in the pig pituitary. RT-PCR with Cthrc1 specific primer pair was performed on mouse pituitary cDNA.

The current study also sheds light on the identity of colloid-filled follicles and the anterior pituitary as a source of Cthrc1. In guinea pigs, the first few colloid follicles of the anterior pituitary are detected at the age of 6 months with an average of just over 4 µm in size (Kameda Y, Cell Tissue Res 263: 115-124). They increase in size and number with age and are found in many vertebrates including humans (Ogawa S, et al., Arch Histol Cytol 59: 467-478; and Kameda Y, Cell Tissue Res 263: 115-124). Here these follicles were identified as well as the pituitary cleft separating the anterior lobe from the pars intermedia as storage sites for Cthrc1. However, not all accumulations of Cthrc1 in the pituitary were encapsulated by folliculostellate cells. Staining of adjacent sections with hematoxylin and eosin indicate that Cthrc1 originates from chromophobe cells (FIG. 5). No expression of Cthrc1 was seen in the pituitary of young adult mice and this raises the question whether the pituitary becomes a more significant provider of Cthrc1 with age when tissue remodeling is limited. Cthrc1 is expressed in many mesenchyme-derived cells during growth and tissue remodeling especially the skeletal system, where it continues to be expressed in adult bone (FIG. 4O), a tissue that constantly undergoes remodeling. With bone mass accounting for a substantial amount of total body mass, it is likely that osteocytes and osteoblasts contribute substantially to circulating Cthrc1 levels. Interestingly, osteocalcin, another hormone derived from osteoblastic cells has recently been shown to regulate glucose metabolism and fat mass (Lee N K, et al., Cell 130: 456-469).

Cthrc1 was identified as a novel circulating hormone with metabolic effects including regulation of lipid storage in liver and heart. These findings are relevant to cardiac dysfunction associated with diabetes and metabolic syndrome. Expression in the hypothalamus, pituitary gland and remodeling tissues are likely to contribute to Cthrc1 plasma levels.

The above examples were carried out with the following materials and methods.

All protocols involving animals were approved by the Institutional Animal Care and Use Committee of the Maine Medical Center (protocol numbers 0905 and 1112) and were in compliance with all applicable regulations and guidelines including the National Institutes of Health *Guide for Care and Use of Laboratory Animals*. All surgical interventions were performed under general anesthesia with tribromoethanol/tert. amyl alcohol. Human plasma samples were obtained under a protocol approved by the Institutional Review Board of the Maine Medical Center (protocol number 3657).

Animals

A novel Cthrc1 null allele was generated by replacing exons 2, 3 and 4 with a neomycin cassette using the targeting vector pKO Scrambler NTKV-1905 (Stratagene) (FIG. 1A). Exon 1 contains only 5' untranslated sequence and the N-terminal 52 amino acids, which include the signal sequence plus additional 20 amino acids. Embryonic stem cell clones were screened by Southern blotting and positive clones injected into blastocysts (FIG. 1B). Two chimeras were obtained and bred with C57BL/6J mice, producing offspring with agouti coat color indicating germ line transmission. Their genotypes were verified by Southern blotting and a PCR screen that amplified the wild-type allele (primers: 5'-CCACTG-GAAACCTCTGGAGTTG-3' (SEQ ID NO: 4) and 5'-AAGTTCACACAAAGGAAGCCCCGC-3' (SEQ ID NO: 5)) and the mutant allele (primers: 5'-GTGTGTTTTGAGGT- GTGGTCCC-3' (SEQ ID NO: 6) and 5'TGGATGTGGAAT-GTGTGCGAGG-3 (SEQ ID NO: 7)). These animals have been backcrossed on the 12956/SvEv or C57BL/6J background for 11 generations.

Pig tissues were obtained from euthanized animals (6 to 12 months of age) of the Advanced Trauma Operative Management (ATOM) courses conducted at our facility or from a local slaughterhouse. Primer sequences used for RT-PCR of pig cDNA were 5'-GACCCCTTCATTGACCTCCACTAC-3' (SEQ ID NO: 8) and 5'-ACATACTCAGCACCAGCATCGC-3' (SEQ ID NO: 9) for Gapdh and 5'-GAATGCCTGAGG-GAAATCTTTGAG-3' (SEQ ID NO: 10) and 5'-CGTCTC-CTTTTGGGTAATCTGCG-3' (SEQ ID NO: 11) for Cthrc1. The annealing temperature was 55.9° C. and 35 cycles of amplification were performed.

Rabbit Monoclonal Antibody Generation, Immunohistochemistry, and Immunoblotting

A rabbit monoclonal antibody was raised against a synthetic peptide of the conserved C terminus of Cthrc1 (GDASTGWNSVSRIIIEELP (SEQ ID NO: 12)) using the services of Epitomics, Inc. (Burlingame, Calif.). Clone Vli-55 was suitable for Western blotting and immunohistochemistry on paraffin-embedded, paraformaldehyde-fixed tissues. Rabbit monoclonal Vli-55 was used at 20 ng/ml for immunohistochemistry on paraffin-embedded, formalin-fixed tissue section following antigen retrieval with citrate buffer (0.1M, pH=6.0). Subsequent steps of the immunostaining procedure were executed as previously published (Larman B W, et al., Cell Signal 24: 257-264). The antibody was conjugated to horse radish peroxidase (Pierce, ThermoFisher) following the manufacturer's protocol and its suitability for Western blotting was validated using plasma samples from Cthrc1 transgenic and wild-type mice (1:2000 dilution as described (Pyagay P, et al., Circ Res 96: 261-268)). Five μl of plasma were loaded per lane and immunoblotting was performed on reduced and denatured samples (FIG. 2). Validation for immunohistochemistry was performed on tissues previously shown to express Cthrc1, i.e. adventitial cells of remodeling arteries, dermal cells in skin seven days after wounding, embryonic cartilage, and absence of staining on tissue sections from Cthrc1 null mice (FIG. 2). Pre-absorption of the antibody with peptide antigen was used as an additional control for specificity.

Cthrc1 in Human Plasma

For detection of human Cthrc1 in plasma, mouse monoclonal antibodies were raised against a synthetic peptide with sequence of the N terminus of human Cthrc1 (SEIP-KGKQKAQLRQRE (SEQ ID NO: 13)) using the hybridoma services of Maine Biotechnology Services (Portland, Me.). Anti-Cthrc1 clones 10G7 and 19C7 detected human Cthrc1 expressed in CHO-K1 cells by indirect ELISA without amplification in the low picogram range. Protein A-purified antibodies were conjugated to magnetic beads (Pierce, ThermoFisher) following the manufacturer's protocol. EDTA plasma was obtained from a healthy volunteer. 15 ml of plasma were incubated overnight at 1° C. with anti-Cthrc1 conjugated magnetic beads, and washed extensively with phosphate buffer prior to elution with 0.1M glycine, pH=2.6. The eluate was immunoblotted with HRP-conjugated monoclonal anti-Cthrc1 antibodies following SDS-PAGE under reducing conditions.

Glycogen Assay

Six month old gender-matched wild-type and Cthrc1 null mice on the C57BL/6J background were used for this assay (n=3-4 animals per group). Samples were obtained from identical sites of the liver and the right quadriceps muscle. Glycogen from 10 mg fresh-frozen tissue was hydrolyzed to glucose in 500 μl of 2N HCl for 2 h at 100° C. with vortexing every 30 minutes. Samples were allowed to cool down before neutralization with 500 μl of 2N NaOH and 50 μl 1M TRIS pH=7.6. The glucose hexokinase reagent (ThermoFisher) was used as directed. A standard curve was established with glucose standards covering the range of 0.00312 to 0.1μ mole. Using GraphPad Prism software, concentrations of glucose in the samples were calculated based on the standard curve. Three different samples from each organ were assayed in duplicates and mean values were calculated, then compared using Student's t-test.

Radioactive Labeling of Cthrc1 Protein with $^{125}$Iodine

An adenovirus was generated expressing rat Cthrc1 with a C terminal myc/6xHis tag ("6xHis" disclosed as SEQ ID NO: 14). CHO-K1 cells were transduced with this adenovirus and Cthrc1 protein was purified from the conditioned medium with HIS-Select affinity gel (Sigma) following the supplier's instructions. Silver-stained SDS-PAGE gels demonstrated >95% purity of the purified protein (not shown). A BCA protein assay (Pierce) was used to determine the concentration of the purified protein. Purified Cthrc1 was labeled with $^{125}$I (Perkin Elmer) using iodination tubes (Pierce). Six μg of radioactive labeled Cthrc1 were infused into adult anesthetized Cthrc1 null mice via the left carotid artery (n=3 mice). Blood samples were obtained at indicated times and Cthrc1 levels were determined in a gamma counter. The half-life in circulation was calculated from the clearance curve using GraphPad Prism software. SDS-PAGE analysis followed by autoradiography was performed on 1 μl of plasma obtained thirty minutes after injection of $^{125}$I-Cthrc1 to verify its integrity. All tissues were harvested six hours after $^{125}$I-Cthrc1 injection following extensive perfusion with lactated Ringer's solution to remove as much blood from organs as possible. $^{125}$I-Cthrc1 per mg wet weight of tissue was measured by gamma counting.

Cell Culture and Western Blotting

HEK293-T and CHO-K1 cells were grown as described and transfected with an expression vector for human Cthrc1 using Fugene6 HD (Roche) (LeClair R J, et al., Circ Res 100: 826-833). 48 hours after transfection the growth medium was replaced with serum-free medium and cell lysates as well as conditioned media were harvested 24 hours later for immunoblotting with HRP conjugated anti-Cthrc1 antibody.

Statistical Analysis

Data are expressed as means±standard deviation. Student's t-test was used for all calculations. P≤0.05 was considered significant.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of treating metabolic syndrome or a metabolic syndrome associated condition in a subject, the method comprising
administering an effective amount of a Collagen Triple Helix Repeat Containing 1 (Cthrc1) polypeptide to the subject, wherein said Cthrc1 polypeptide is at least 95% identical to SEQ ID NO: 1, thereby treating metabolic syndrome.

2. The method of claim 1, wherein said metabolic syndrome associated condition is selected from the group consisting of type II diabetes, hyperlipidemia, elevated triglycerides, elevated blood pressure or hypertension, hyperglycemia, and obesity.

3. The method of claim 1, wherein said method further comprises reducing excess lipid and increasing glycogen storage in a tissue or organ of a subject.

4. The method of claim 3, wherein the effective amount of Cthrc1 is sufficient to reduce lipids in target organs by at least 40%.

5. The method of claim 1, wherein said method further comprises treating steatosis in a subject.

6. The method of claim 5, wherein the steatosis is selected from the group consisting of hepatic steatosis and cardiac steatosis.

7. The method of claim 1, wherein the polypeptide is administered systemically.

8. The method of claim 1, wherein the method reduces the risk of heart disease or diabetes.

9. The method of claim 1, wherein the method comprises identifying the subject as having a metabolic syndrome or an associated condition.

* * * * *

UNITED STATES PATENT AND TRADEMARK OFFICE
CERTIFICATE OF CORRECTION

| | |
|---|---|
| PATENT NO. | : 9,050,296 B2 |
| APPLICATION NO. | : 13/934455 |
| DATED | : June 9, 2015 |
| INVENTOR(S) | : Volkhard Lindner et al. |

It is certified that error appears in the above-identified patent and that said Letters Patent is hereby corrected as shown below:

In The Specification

At column 1, lines 15-17, the sentence, "This work was supported by the following grants from the from the National Center for Research Resources, Grant Nos.: HL69182 and P20 RR-15555." should read: "This invention was made with government support under grant number HL069182, awarded by the National Center for Research Resources and under grant number P20RR015555, awarded by the National Center for Research Resources."

Signed and Sealed this
Sixteenth Day of August, 2016

Michelle K. Lee
*Director of the United States Patent and Trademark Office*